(12) United States Patent
Ono et al.

(10) Patent No.: US 8,643,710 B2
(45) Date of Patent: Feb. 4, 2014

(54) IMAGE PICKUP APPARATUS

(71) Applicant: Olympus Medical Systems Corp., Tokyo (JP)

(72) Inventors: Wataru Ono, Hachioji (JP); Hidenori Hashimoto, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/681,839

(22) Filed: Nov. 20, 2012

(65) Prior Publication Data
US 2013/0169843 A1 Jul. 4, 2013

Related U.S. Application Data

(63) Continuation of application No. PCT/JP2011/072473, filed on Sep. 29, 2011.

(30) Foreign Application Priority Data

Sep. 30, 2010 (JP) ................. 2010-221925

(51) Int. Cl.
*A61B 1/04* (2006.01)
(52) U.S. Cl.
USPC ............... 348/68; 348/65; 348/234; 348/235; 600/101; 600/109; 600/177
(58) Field of Classification Search
USPC .................... 600/101, 109, 114, 118; 348/45, 348/62–161, 207.1–376
See application file for complete search history.

(56) References Cited

U.S. PATENT DOCUMENTS

| | | | |
|---|---|---|---|
| 8,231,522 B2* | 7/2012 | Endo et al. | 600/109 |
| 2003/0176768 A1* | 9/2003 | Gono et al. | 600/109 |
| 2007/0016077 A1 | 1/2007 | Nakaoka et al. | |
| 2009/0058999 A1 | 3/2009 | Gono et al. | |
| 2010/0188491 A1 | 7/2010 | Shizukuishi | |

FOREIGN PATENT DOCUMENTS

| | | |
|---|---|---|
| JP | 63-167577 A | 7/1988 |
| JP | 2001-190488 A | 7/2001 |
| JP | 2002-95635 A | 4/2002 |
| JP | 2006-187598 A | 7/2006 |
| JP | 2006-341077 A | 12/2006 |
| JP | 2010-193421 A | 9/2010 |

OTHER PUBLICATIONS

International Search Report PCT/JP2011/072473 dated Dec. 27, 2011.

* cited by examiner

*Primary Examiner* — Sath V Perungavoor
*Assistant Examiner* — Nathnael Aynalem
(74) *Attorney, Agent, or Firm* — Scully, Scott, Murphy & Presser, P.C.

(57) ABSTRACT

An image pickup apparatus includes first and second irradiation units that emit first light and second light, respectively, an image pickup unit that outputs, as pixel information, an electrical signal after photoelectric conversion from a pixel arbitrarily designated as a read target among pixels, a setting unit that arbitrarily sets a pixel as the read target and a read order in the image pickup unit, a control unit that controls irradiation processes in the first and second irradiation units and changes the pixel as the read target and the read order according to a type of an irradiation unit that emits light, a reading unit that reads the pixel information by causing the pixel information to be output from the pixel set as the read target, in accordance with the read order, and an image processing unit that generates an image from the pixel information read by the reading unit.

15 Claims, 19 Drawing Sheets

IMAGE PICKUP APPARATUS

CROSS REFERENCES TO RELATED APPLICATIONS

This application is a continuation of PCT International Application Ser. No. PCT/JP2011/072473 filed on Sep. 29, 2011 which designates the United States, incorporated herein by reference, and which claims the benefit of priority from Japanese Patent Applications No. 2010-221925, filed on Sep. 30, 2010, incorporated herein by reference.

BACKGROUND OF THE INVENTION

1. Field of the Invention

The present invention relates to an image pickup apparatus that includes an image pickup unit capable of outputting, as pixel information, an electrical signal after photoelectric conversion from a pixel arbitrarily designated as a read target among a plurality of pixels for imaging.

2. Description of the Related Art

Conventionally, in the medical field, endoscope systems are used when observing the inside of organs of a subject. In an endoscope system, typically, an in-vivo image is picked up by inserting an elongated flexible insertion unit into the body cavity of a subject, such as a patient, emitting the white light to a living tissue in the body cavity via the inserted insertion unit, and receiving the reflected light by the image pickup unit at the tip of the insertion unit. The in-vivo image picked up in this manner is displayed on the monitor of this endoscope system. A user, such as a doctor, observes the inside of the body cavity of the subject via the in-vivo image displayed on the monitor of the endoscope system.

In the endoscope field, a narrow band imaging system has been proposed that uses the special illumination light whose spectral characteristics are narrow-banded compared with the white illumination light used in a conventional RGB frame sequential system (for example, see Japanese Patent Application Laid-open No. 2002-095635). In the narrow band imaging system, capillary vessels in mucosal surface layers and pit patterns are enhanced by emitting light in two bands, i.e., narrow-banded blue light and green light that are easily absorbed by hemoglobin in blood, which contributes to the early detection of bleeding sites or tumor sites that are sites to be detected. Moreover, a fluorescent substance that is originally present in a living tissue and has a spectrum in the range of green or red or a labeling substance that is introduced into the subject and emits red fluorescence or green fluorescence is detected by emitting blue excitation light or violet excitation light having a shorter wavelength than blue.

SUMMARY OF THE INVENTION

An image pickup apparatus according to one aspect of the present invention includes: a first irradiation unit that emits first light to a subject; a second irradiation unit that emits second light that has a wavelength band different from that of the first light, to the subject; an image pickup unit that is capable of outputting, as pixel information, an electrical signal after photoelectric conversion from a pixel arbitrarily designated as a read target among a plurality of pixels for imaging; a setting unit that is capable of arbitrarily setting a pixel as the read target and a read order in the image pickup unit; a control unit that controls irradiation processes in the first irradiation unit and the second irradiation unit and changes the pixel as the read target and the read order set by the setting unit according to a type of an irradiation unit that emits light; a reading unit that reads the pixel information by causing the pixel information to be output from the pixel set as the read target by the setting unit among the plurality of pixels for imaging in the image pickup unit, in accordance with the read order according to setting in the setting unit; an image processing unit that generates an image from the pixel information read by the reading unit; and a display unit that displays the image generated by the image processing unit. In a frame in which the image pickup unit picks up an image of the subject irradiated with the second light emitted from the second irradiation unit to output the pixel information, the control unit performs control such that the reading unit does not read the pixel information from a first pixel on which light corresponding to the wavelength band of the second light is not incident and the reading unit reads the pixel information from a second pixel on which light corresponding to the wavelength band of the second light is incident during a period for reading the first pixel.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 1:
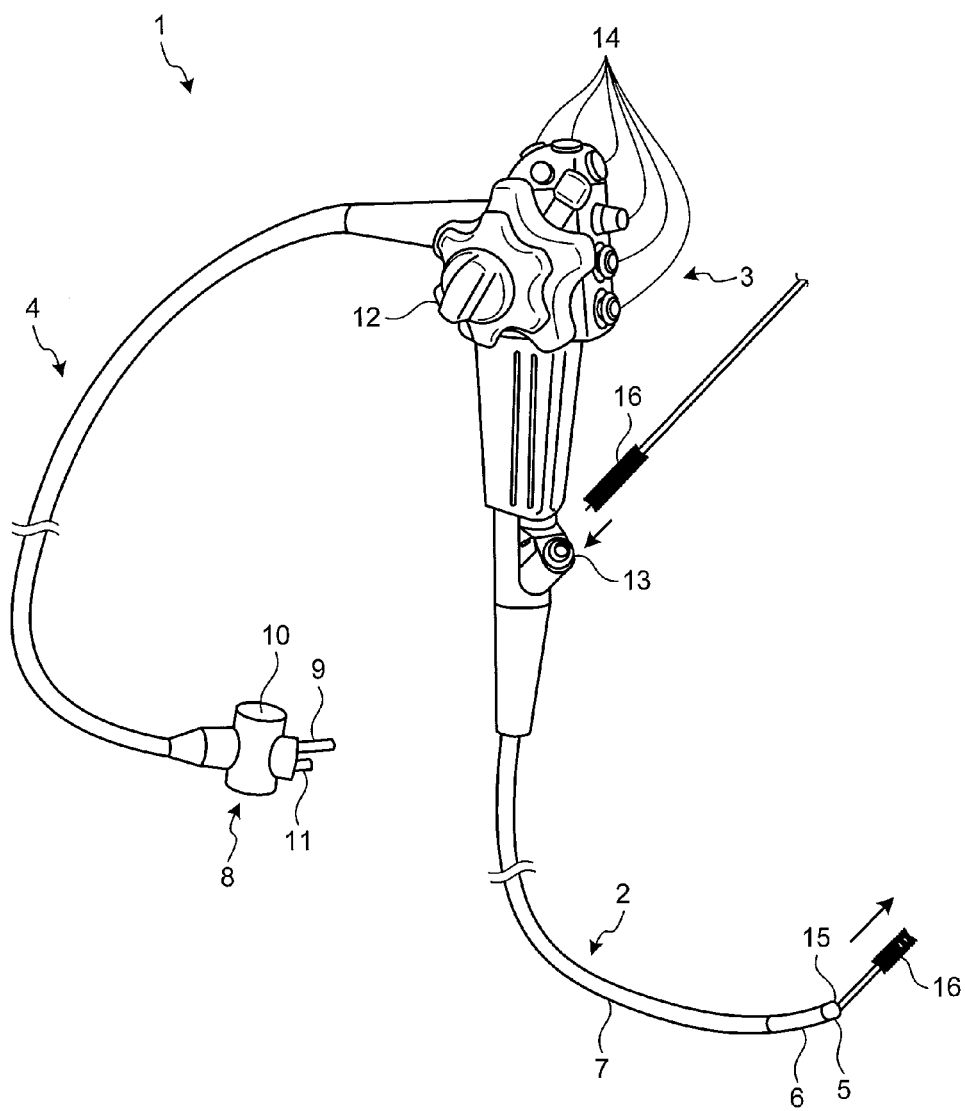
FIG. 1 is a diagram illustrating a schematic configuration of an endoscope part according to a first embodiment.

A medical endoscope system that includes an image pickup unit at the tip of an insertion unit and picks up and displays an image in a body cavity of a subject, such as a patient, will be explained below as embodiments according to the present invention. The present invention is not limited to the embodiments. In the description of the drawings, the same components are denoted by the same reference numerals. It should be noted that the drawings are schematic and a relation between the thickness and the width of each component, a ratio of each component, and the like may be different from those in reality. Between the drawings, some portions have a different relation and ratio of dimensions.

First Embodiment

First, an endoscope system according to the first embodiment will be explained. FIG. 1 is a diagram illustrating a schematic configuration of the endoscope part of the endoscope system according to the first embodiment. As shown in FIG. 1, an endoscope 1 in the first embodiment includes an elongated insertion unit 2, an operating unit 3 that is provided at the base end side of the insertion unit 2 and is grasped by an endoscope apparatus operator, and a flexible universal code 4 extending from the side portion of the operating unit 3. The universal code 4 includes therein light guide cables, electrical system cables, and the like.

The insertion unit 2 includes a tip portion 5 that includes therein a CMOS sensor as an image pickup element, a bending portion 6 that is composed of a plurality of bending pieces and can be freely bent, and an elongated flexible tube portion 7 that is provided at the base end side of the bending portion 6 and has a flexibility.

A connector unit 8 is provided at the end portion of the universal code 4. The connector unit 8 includes a light guide connector 9 detachably connected to a light source device, an electrical contact unit 10 that is connected to a control device for transmitting an electrical signal of a subject image, which is photoelectrically converted in the CMOS sensor, to a control device for a signal processing, an air sending cap 11 for sending air to the nozzle of the tip portion 5, and the like. The light source device includes a white light source, a special light source, and the like and supplies light from the white light source or the special light source to the endoscope 1 connected via the light guide connector 9 as illumination light. Moreover, the control device is a device, which supplies power to the image pickup element and to which a photoelectrically converted electrical signal is input from the image pickup element, and the control device processes the electrical signal imaged by the image pickup element, causes a connected display unit to display an image, and outputs a drive signal that performs control, such as a gain adjustment, of the image pickup element and driving of the image pickup element.

The operating unit 3 includes a bending knob 12 that bends the bending portion 6 in the vertical direction and the horizontal direction, a treatment tool insertion portion 13, from which a treatment tool 16, such as a biopsy forceps and a laser probe, is inserted into a body cavity, and a plurality of switches 14 that perform operations of peripheral devices, such as the control device, the light source device, or a unit for sending air, water, and gas. The treatment tool 16 inserted from the treatment tool insertion portion 13 emerges from an opening 15 at the tip of the insertion unit 2 via a treatment tool channel provided inside. For example, when the treatment tool 16 is a biopsy forceps, a biopsy to take an affected tissue by the biopsy forceps, or the like is performed.

Figure 2:
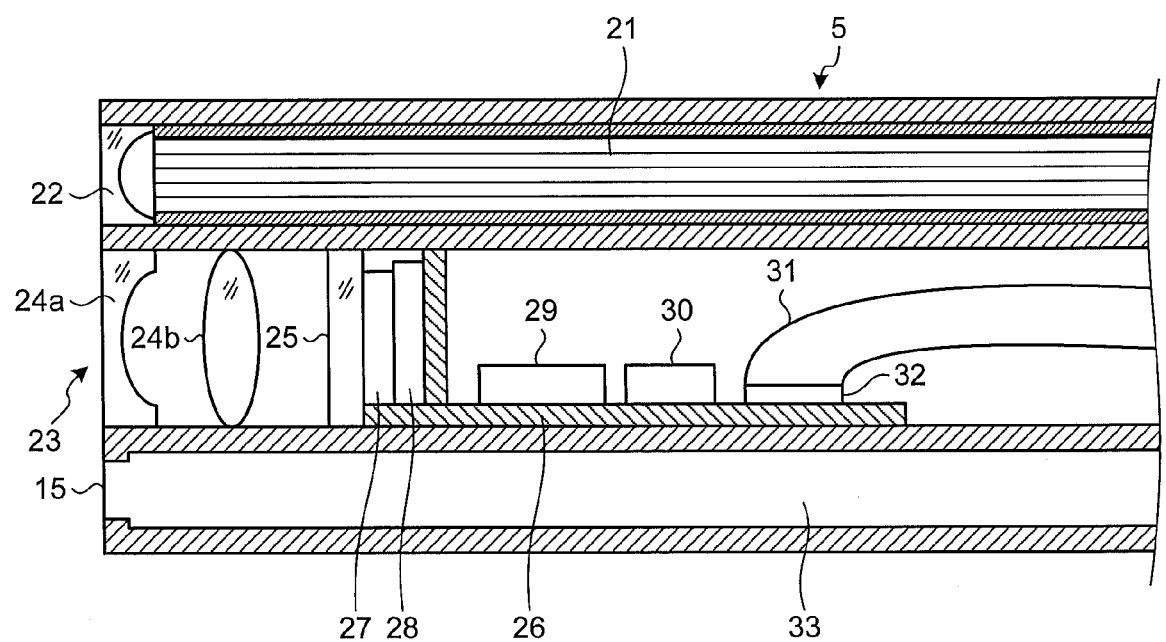
FIG. 2 is a cross-sectional view schematically explaining an internal configuration of a tip portion of an endoscope body portion illustrated in FIG. 1.

Next, the configuration of the tip portion 5 of the insertion unit 2 will be explained. FIG. 2 is a cross-sectional view schematically explaining an internal configuration of the tip portion 5 of the endoscope 1 illustrated in FIG. 1. As shown in FIG. 2, at the tip of the tip portion 5 of the endoscope 1, the opening 15 for causing the treatment tool to emerge, which communicates with an illumination lens 22, an observation window 23, and a treatment tool channel 33, and an air-sending and water-sending nozzle (not shown) are provided.

The white light or the special light supplied from the light source device via a light guide 21, which is composed of a glass fiber bundle or the like, is emitted from the illumination lens 22. At the observation window 23, a light receiving unit 28, which includes a plurality of pixels for imaging arranged two-dimensionally in a matrix form, is arranged at an image forming position of the optical system composed of lenses 24a and 24b. The light receiving unit 28 receives light entered via the optical system composed of the lenses 24a and 24b and picks up an image inside the body cavity. On the light receiving surface side of the light receiving unit 28, a cover glass 25 is provided. An on-chip filter 27, in which R, G, and B filters are arrayed corresponding to the pixel array in the light receiving unit 28, is provided between the cover glass 25 and the light receiving unit 28. The light receiving unit 28 is mounted on a circuit board 26 together with an IC 29 that indicates the imaging timing to the light receiving unit 28 and reads an image signal obtained by the light receiving unit 28 and converts the image signal to an electrical signal, a chip capacitor 30, and the like. An electrode 32 is provided on the circuit board 26. The electrode 32 is connected to an assembled cable 31 that transmits an electrical signal to the control device, for example, via an anisotropic conductive resin film. The assembled cable 31 includes a plurality of signal lines, such as signal lines that transmit an image signal that is an electrical signal output from the light receiving unit 28 and signal lines that transmit a control signal from the control device.

Figure 3:
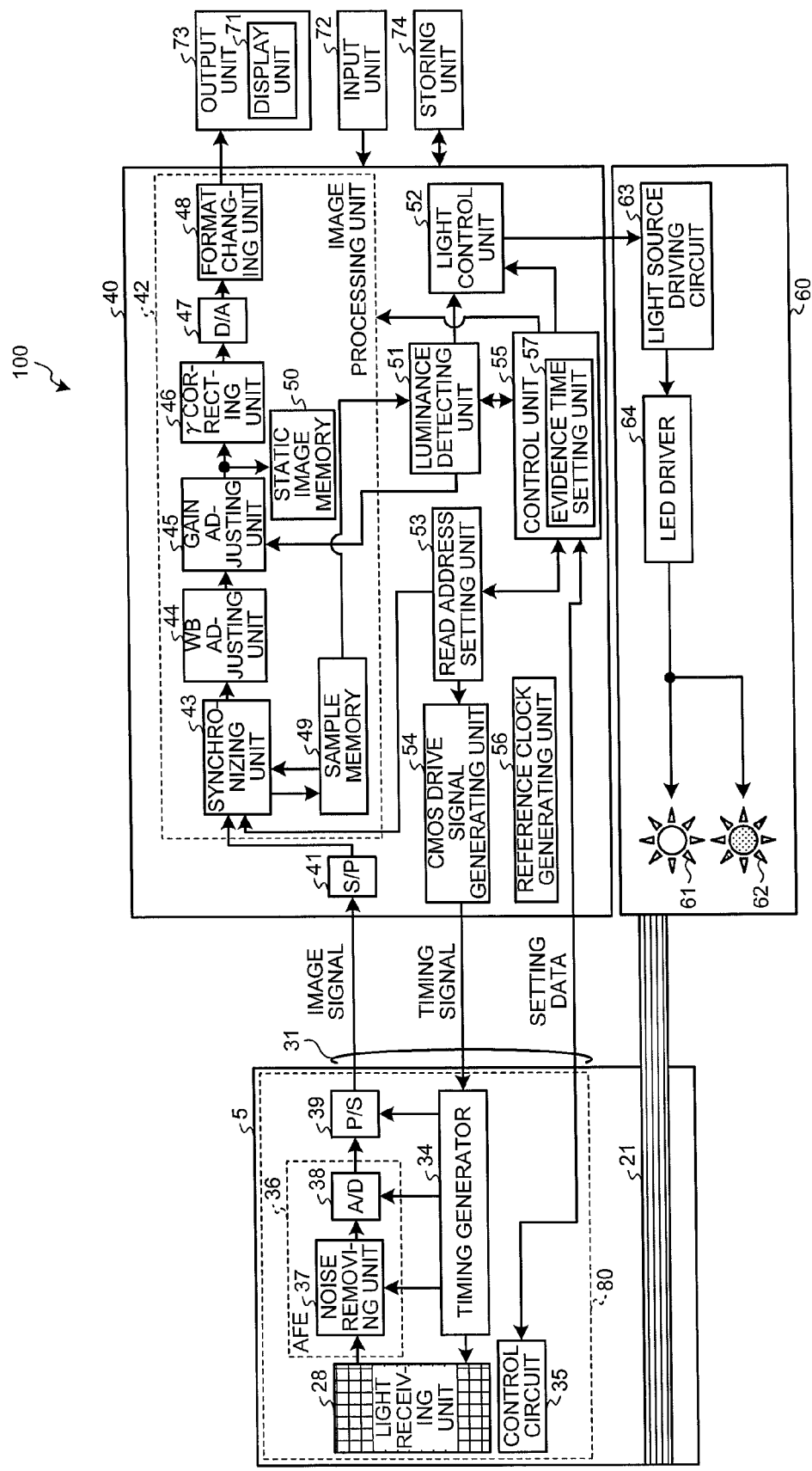
FIG. 3 is a block diagram illustrating a schematic configuration of an endoscope system according to the first embodiment.

Next, the configuration of the endoscope system according to the first embodiment will be explained. FIG. 3 is a block diagram illustrating a configuration of the endoscope system according to the first embodiment. As shown in FIG. 3, an endoscope system 100 according to the first embodiment includes a control device 40 that is connected to a CMOS image pickup element 80 provided in the tip portion 5 via the assembled cable 31 including a plurality of signal lines, a light source device 60 that supplies the white light or the special light, a display unit 71 that displays an in-vivo image picked up by the CMOS image pickup element 80, an output unit 73 that outputs information on in-vivo observation, an input unit 72 that inputs various instruction information required for in-vivo observation, and a storing unit 74 that stores in-vivo images and the like.

The CMOS image pickup element 80 is provided in the tip portion 5. The CMOS image pickup element 80 includes the light receiving unit 28, a control circuit 35, a timing generator 34, an AFE (Analog Front End) unit 36 that includes a noise removing unit 37 and an A/D converting unit 38, and a P/S converting unit 39 that converts an input digital signal from a parallel form to a serial form. The light receiving unit 28 and the CMOS sensor peripheral circuits composing the CMOS image pickup element 80 are, for example, integrated into a single chip.

The light receiving unit 28 outputs, as pixel information, an electrical signal after photoelectric conversion from a pixel arbitrarily designated as a read target among a plurality of pixels for imaging arranged two-dimensionally in a matrix form. Each pixel information includes a luminance value. The control circuit 35 controls the imaging process to the light receiving unit 28, the imaging speed of the light receiving unit 28, the read process of the pixel information from a pixel in the light receiving unit 28, and the transmission process of the read pixel information in accordance with the setting data output from the control device 40.

The timing generator 34 is driven in accordance with the timing signal output from the control device 40 and causes an electrical signal after photoelectric conversion to be output, as the pixel information, from a pixel at a position (address) designated as a read target among a plurality of pixels composing the light receiving unit 28 in accordance with the read order according to the setting in a read address setting unit 53.

The noise removing unit 37 removes the noise in a signal of the pixel information output from a predetermined pixel in the light receiving unit 28. The A/D converting unit 38 converts the signal of the pixel information from which the noise is removed from an analog signal to a digital signal and outputs it to the P/S converting unit 39. The pixel information read from the light receiving unit 28 by the timing generator 34 and the AFE unit 36 is transmitted to the control device 40 via a predetermined signal line of the assembled cable 31 as an image signal in a serial form converted by the P/S converting unit 39.

The control device 40 processes image signals and causes the display unit 71 to display an in-vivo image and controls each component of the endoscope system 100. The control device 40 includes an S/P converting unit 41, an image processing unit 42, a luminance detecting unit 51, a light control unit 52, the read address setting unit 53, a CMOS drive signal generating unit 54, a control unit 55, and a reference clock generating unit 56.

The S/P converting unit 41 converts an image signal that is a digital signal received from the tip portion 5 from a serial form to a parallel form.

The image processing unit 42 generates an in-vivo image to be displayed on the display unit 71 on the basis of the addresses of pixels in the light receiving unit 28, which are read by the timing generator 34 and the AFE unit 36, from image signals in a parallel form output from the S/P converting unit 41, i.e., the pixel information on the pixels read by the timing generator 34 and the AFE unit 36.

The image processing unit 42 includes a synchronizing unit 43, a WB adjusting unit 44, a gain adjusting unit 45, a γ correcting unit 46, a D/A converting unit 47, a format changing unit 48, a sample memory 49, and a static image memory 50.

The synchronizing unit 43 inputs an input image signal of each of an R pixel, a G pixel, and a B pixel in a memory (not shown) provided for each pixel, associates the image signals with the addresses of the pixels in the light receiving unit 28 read by the timing generator 34 and the AFE unit 36, and stores values in each memory while sequentially updating the values with each input image signal, and moreover, the synchronizing unit 43 synchronizes the image signals in the three memories as RGB image signals. The synchronized RGB image signals are sequentially output to the WB adjusting unit 44 and some of the synchronized RGB image signals are output also to the sample memory 49 for image analysis, such as luminance detection, and are stored in the sample memory 49.

The WB adjusting unit 44 adjusts the white balance of RGB image signals. The gain adjusting unit 45 adjusts the gain of RGB image signals. The γ correcting unit 46 performs gradation conversion on RGB image signals to correspond to the display unit 71.

The D/A converting unit 47 converts RGB image signals after gradation conversion from a digital signal to an analog signal. The format changing unit 48 changes the image signals converted to an analog signal to a format, such as a Hi-Vision system, and outputs them to the display unit 71. As a result, one in-vivo image is displayed on the display unit 71. Some of the RGB image signals whose gain is adjusted by the gain adjusting unit 45 are stored also in the static image memory 50 for displaying a static image, displaying an enlarged image, or displaying an enhanced image.

The luminance detecting unit 51 detects the luminance level corresponding to each pixel from RGB image signals stored in the sample memory 49 and stores the detected luminance levels in a memory provided in the luminance detecting unit 51. Moreover, the luminance detecting unit 51 calculates the gain adjustment value and the exposure dose on the basis of the detected luminance levels. The calculated gain adjustment value is output to the gain adjusting unit 45 and the calculated exposure dose is output to the light control unit 52. Furthermore, the detection result by the luminance detecting unit 51 is output also to the control unit 55.

The light control unit 52 sets the amount of current to be supplied to each light source and the drive condition of a neutral density filter and outputs a light source synchronizing signal including a setting condition to the light source device 60 on the basis of the exposure dose output from the luminance detecting unit 51 under the control of the control unit 55. The light control unit 52 sets the type, the light intensity, and the light emission timing of the light emitted from the light source device 60.

The read address setting unit 53 can arbitrarily set pixels as a read target and the read order in the light receiving unit 28. In other words, the read address setting unit 53 can arbitrarily set the addresses of pixels in the light receiving unit 28 to be read by the timing generator 34 and the AFE unit 36. Moreover, the read address setting unit 53 outputs the set addresses of pixels as a read target to the synchronizing unit 43.

The CMOS drive signal generating unit 54 generates a timing signal for driving the light receiving unit 28 and the CMOS sensor peripheral circuits, and outputs it to the timing generator 34 via a predetermined signal line in the assembled cable 31. This timing signal includes the addresses of pixels as a read target.

The control unit 55, which is composed of a CPU or the like, reads various programs stored in a not-shown memory and performs various process procedures described in the programs, thereby performing drive control of each component, input/output control of information on each component, and information processing for inputting and outputting various information between the components. The control device 40 outputs setting data for controlling imaging to the control circuit 35 in the tip portion 5 via a predetermined signal line in the assembled cable 31. The setting data includes instruction information indicating the imaging speed of the light receiving unit 28 and the read speed of the pixel information from arbitrary pixels in the light receiving unit 28, transmission control information on the read pixel information, and the like. The control unit 55 controls the irradiation process in a white light source 61 and a special light source 62 and changes pixels as a read target and the read order set by the read address setting unit 53 in accordance with the type of the light source that emits light.

The reference clock generating unit 56 generates a reference clock signal to be an operation reference of each component of the endoscope system 100 and supplies the generated reference clock signal to each component of the endoscope system 100.

The light source device 60 performs the light irradiation process under the control of the control unit 55. The light source device 60 includes the white light source 61 that is composed of an LED or the like and emits the white illumination light, the special light source 62 that emits light of any of R, G, and B, which is the light having a wavelength band different from the white illumination light and is narrow-banded by a narrow bandpass filter, as the special light, a light source driving circuit 63 that controls the amount of current to be supplied to the white light source 61 or the special light source 62 and driving of the neutral density filter in accordance with the light source synchronizing signal transmitted from the light control unit 52, and an LED driver 64 that supplies a predetermined amount of current to the white light source 61 or the special light source 62 under the control of the light source driving circuit 63. The light emitted from the white light source 61 or the special light source 62 is supplied to the insertion unit 2 via the light guide 21 and is emitted to the outside from the tip of the tip portion 5. The special light source 62, for example, emits the NBI illumination light in two bands, i.e., narrow-banded blue light and green light that are easily absorbed by hemoglobin in blood.

The endoscope system 100 according to the first embodiment does not read image signals corresponding to all the pixels in the light receiving unit 28 but reads image signals corresponding to only pixels at the addresses arbitrarily set by the read address setting unit 53 under the control of the control unit 55. Then, in the endoscope system 100, the luminance values of pixels corresponding to the wavelength band of the light emitted from the light source are increased by changing pixels as a read target and the read order in the light receiving unit 28 in accordance with the type of the light source that emits light, thereby obtaining an appropriate image regardless of the type of the light source.

Figure 4:
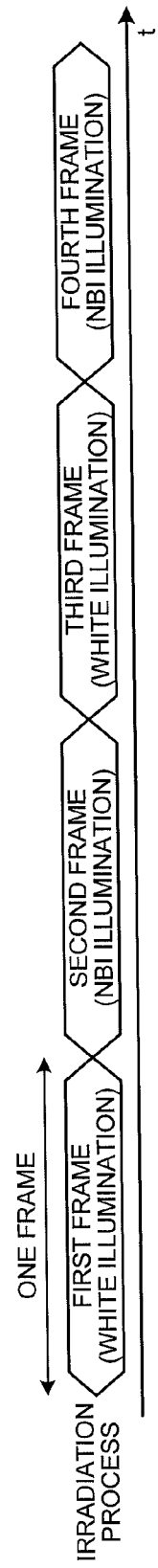
FIG. 4 is a diagram explaining an irradiation process by a white light source and a special light source illustrated in FIG. 3.

In the CMOS image pickup element 80, pixels as a read target can be changed per frame. In the first embodiment, as shown in FIG. 4, the control unit 55 causes the white light source 61 and the special light source 62 to emit light alternately. The control unit 55 includes an irradiation time setting unit 57 that sets the irradiation time for each irradiation by each light source to correspond to the time required for outputting the pixel information corresponding to one image by the CMOS image pickup element 80, and controls the white light source 61 and the special light source 62 in accordance with the setting by the irradiation time setting unit 57. Furthermore, the control unit 55 obtains a normal image by white irradiation and an NBI image by the NBI illumination light at the same time by changing pixels as a read target and the read order per frame in accordance with the type of the light source that emits light.

At this time, in the frame in which the pixel information is output by picking up an image of a subject that is irradiated with the special light emitted from the special light source 62, the control unit 55 controls the read timing of the timing generator 34 such that the exposure time of G and B pixels, on which the light corresponding to the wavelength band of the NBI illumination light is incident, becomes longer than the exposure time in the case where all the pixels are read, thereby improving the luminance values of G and B pixels in the light receiving unit 28 that receives narrow-banded blue light and green light that are the special light.

Figure 5:
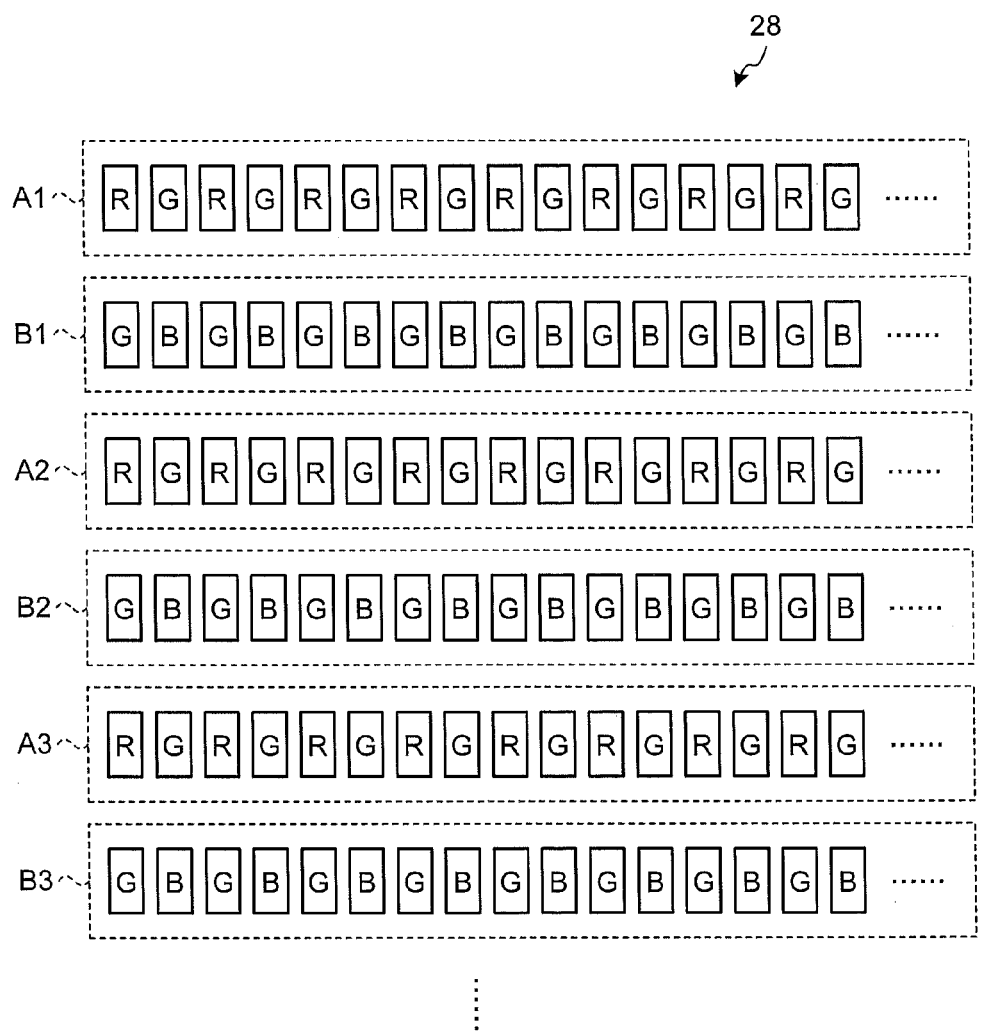
FIG. 5 is a diagram explaining an example of a pixel array in a light receiving unit illustrated in FIG. 3.

Next, the read process according to the first embodiment will be explained with reference to FIG. 5 to FIG. 9. First, an example of the pixel array in the light receiving unit 28 is explained. FIG. 5 is a diagram explaining an example of the pixel array in the light receiving unit 28. FIG. 5 illustrates only part of the light receiving unit 28. In the light receiving unit 28, for example, a line in which an R pixel and a G pixel are alternately located and a line in which a G pixel and a B pixel are alternately located are alternately arranged as in lines A1 to A3 and lines B1 to B3. In the example in FIG. 5, one pixel is composed of vertically and horizontally adjacent R, G, G, and B pixels. The timing generator 34 reads the pixel information on each pixel in units of lines in sequence following the direction from left to right in FIG. 5.

Figure 6:
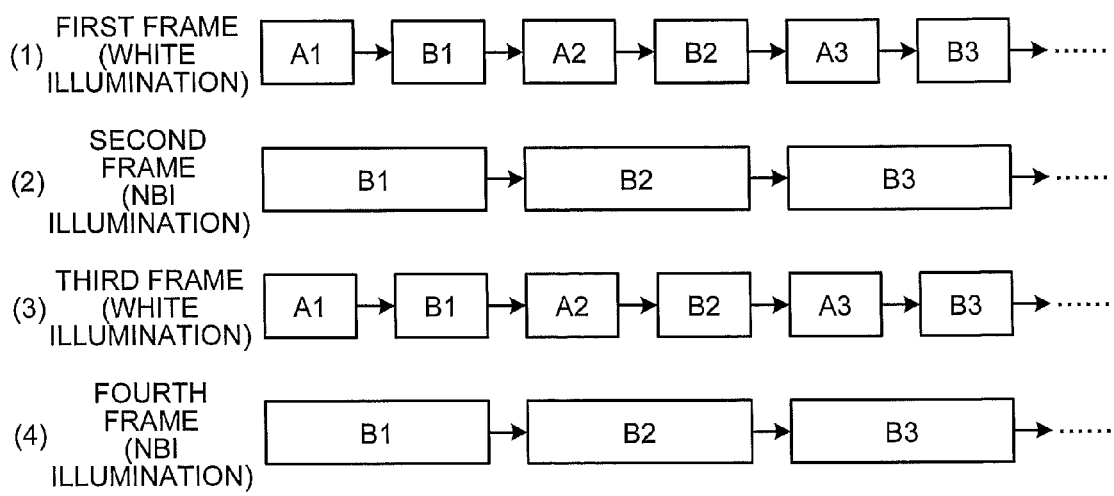
FIG. 6 is a diagram explaining a read process by a timing generator illustrated in FIG. 3.
Figure 7:
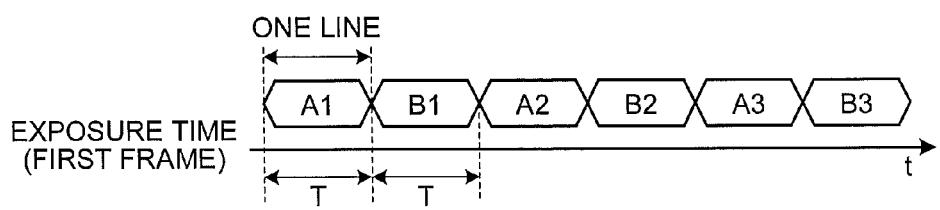
FIG. 7 is a diagram explaining an exposure time of each line in the light receiving unit in a frame corresponding to a time slot in which the white light source illustrated in FIG. 3 emits the white illumination light.

The control unit 55 causes the timing generator 34 to perform the read process on all the lines in sequence following a predetermined direction in the first frame corresponding to the time slot in which the white light source 61 emits the white illumination light. As shown in FIG. 6(1), the control unit 55 causes the timing generator 34 to read the pixel information from the lines A1, B1, A2, B2, A3, and B3 in the sequence they appear in the sentence. At this time, as shown in FIG. 7, the exposure time of each line is time T.

In the second frame corresponding to the time slot in which the special light source 62 emits the NBI illumination light, green light and blue light corresponding to the wavelength band of the NBI illumination light are not incident on an R pixel at which a filter that passes therethrough only red light is arranged. Therefore, in the second frame, the control unit 55 causes the timing generator 34 to read the pixel information on the lines B1, B2, and B3 (see FIG. 6(2)), in which only G pixels and B pixels, on which the light corresponding to the wavelength band of the NBI illumination light is incident, are located, in sequence following a predetermined direction. In other words, the control unit 55 does not cause the timing generator 34 to read the pixel information on an R pixel, on which the light corresponding to the wavelength band of the NBI illumination light is not incident, and causes the timing generator 34 to read only the pixel information on G and B pixels.

Figure 8:
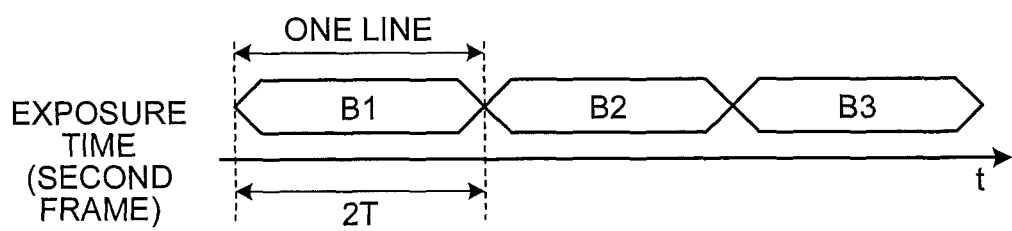
FIG. 8 is diagram explaining an exposure time of each line in the light receiving unit in a frame corresponding to a time slot in which the special light source illustrated in FIG. 3 emits the special light.

In this case, because only half of all the lines are read, the exposure time per line can be extended. In other words, each exposure time of the lines B1, B2, and B3, in which G and B pixels are located, can be made longer than the exposure time in the case where all the pixels are read. Thus, the control unit 55 sets each exposure time of the lines B1, B2, and B3 to be longer than the exposure time in the case where all the pixels are read by controlling the read timing in the read process in the timing generator 34. In the case of the pixel array shown in FIG. 5, the lines are read excluding the lines A1, A2, and A3, in which R and G pixels are located, therefore, as shown in FIG. 8, the exposure time of the lines B1, B2, and B3, in which G and B pixels are located, can be extended to be up to twice the exposure time T per line shown in FIG. 7.

Figure 9:
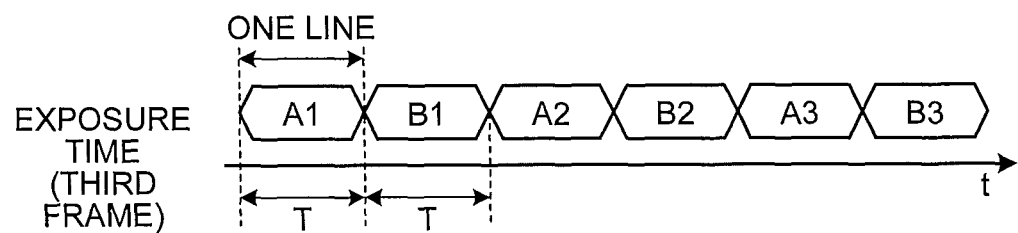
FIG. 9 is a diagram explaining an exposure time of each line in the light receiving unit in a frame corresponding to a time slot in which the white light source illustrated in FIG. 3 emits the white illumination light.

In the third frame corresponding to the time slot in which the white illumination light is emitted, in a similar manner to the first frame, the control unit 55 causes the timing generator 34 to read the pixel information on all the lines from the lines A1, B1, A2, B2, A3, and B3 in the sequence they appear in the sentence (see FIG. 6(3)). In the case also, in a similar manner to the first frame, as shown in FIG. 9, the exposure time of each line is the time T.

Next, in the fourth frame corresponding to the time slot in which the NBI illumination light is emitted, in a similar manner to the second frame, the control unit 55 causes the timing generator 34 to read the pixel information on the lines B1, B2, and B3, in which only G pixels and B pixels are located (see FIG. 6(4)). In this case also, in a similar manner to the second frame, the exposure time of the lines B1, B2, and B3 can be extended to be up to twice the exposure time T compared with the third frame. In the subsequent frames, in a similar manner, setting of the read timing and pixels as a read target is changed in accordance with to the irradiation unit that emits light.

Figure 10:
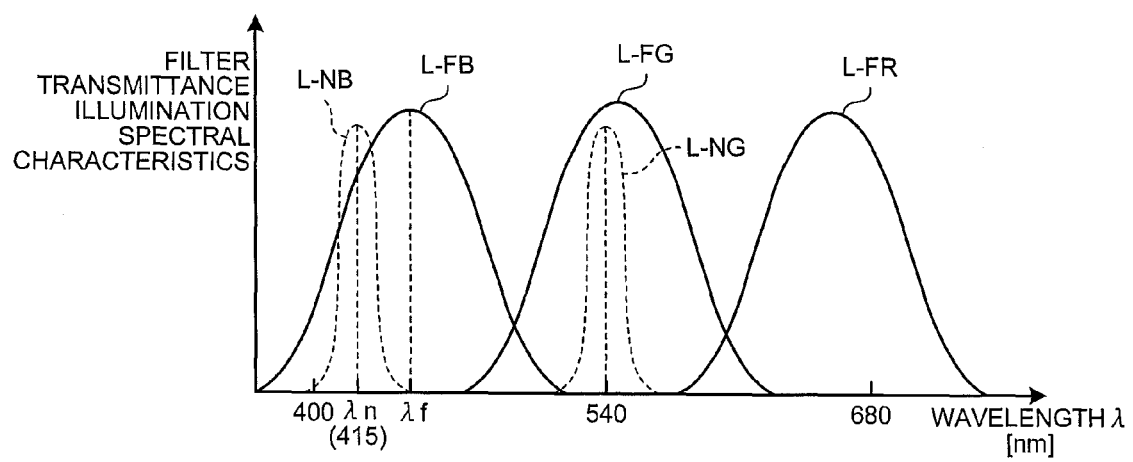
FIG. 10 is a diagram illustrating spectral characteristics of the special light by the special light source and the transmittance of each wavelength of an on-chip filter.

FIG. 10 is a diagram illustrating spectral characteristics of the special illumination light and the transmittance of each wavelength of the on-chip filter 27. A curved line L-FB in FIG. 10 indicates the transmittance of a B filter, a curved line L-FG indicates the transmittance of a G filter, and a curved line L-FR indicates the transmittance of an R filter. As indicated by the curved line L-FB, the B filter passes therethrough the light having a wavelength of about 400 to 500 nm. As indicated by the curved line L-FG, the G filter passes therethrough the light having a wavelength of about 500 to 570 nm. As indicated by the curved line L-FR, the R filter passes therethrough the light having a wavelength of about 610 to 780 nm. Then, as shown in FIG. 10, the special light source 62 emits blue light narrow-banded to the wavelength range of about 400 to 430 nm indicated by a curved line L-NB and green light narrow-banded to the wavelength range of about 530 to 550 nm indicated by a curved line L-NG as the NBI illumination light. Conventionally, specially, in terms of blue light in the special light, the peak wavelength $\lambda n$ (about 415 nm) of the NBI illumination light and the peak wavelength $\lambda f$ (about 460 nm) of the transmittance of the filter do not match, therefore, the luminance value of a B pixel in the light receiving unit that receives blue light cannot be ensured in some cases.

In contrast, in the endoscope system 100 according to the first embodiment, in the frame in which the pixel information is output by picking up an image of a subject that is irradiated with the special light emitted from the special light source 62, only G and B pixels, on which the light corresponding to the wavelength band of the NBI illumination light is incident, are read for the exposure time longer than the exposure time in the case where all the pixels are read. As a result, in the first embodiment, it is possible to increase the luminance values of G and B pixels in the light receiving unit 28, which receives blue light and green light, without providing a dedicated image pickup element, which is conventionally needed, therefore, a light NBI image can be obtained.

Explanation is given of an example of the NBI illumination light in two bands, i.e., narrow-banded blue light and green light, as the special light emitted by the special light source 62, however, it is of course not limited thereto. For example, in order to detect a labeling substance that is introduced into a subject and emits red fluorescence or green fluorescence or a fluorescent substance that is originally present in a living tissue and has a spectrum in the range of green or red, the special light source 62 emits blue excitation light or violet excitation light having a shorter wavelength than blue. In this case, in the frame in which the pixel information is output by picking up an image of a subject that is irradiated with the special light emitted from the special light source 62, the control unit 55 causes the timing generator 34 to read only the lines A1, A2, and A3 (see FIG. 5), in which R and G pixels, on which red light or green light corresponding to the wavelength band of red fluorescence or green fluorescence as a target to be detected is incident, are located. Furthermore, the control unit 55 controls the read timing in the read process in the timing generator 34 such that the exposure time of R and G pixels, on which red light or green light corresponding to the wavelength band of red fluorescence or green fluorescence as a target to be detected is incident, becomes longer than the exposure time in the case where all the pixels are read. Consequently, it is possible to increase the luminance values of R and G pixels in the light receiving unit 28 that receives narrow-banded red light and green light that are the special light.

Moreover, when the special light source 62 emits the special light in two bands, i.e., narrow-banded red light and green light, in the frame in which the pixel information is output by picking up an image of a subject that is irradiated with the special light emitted from the special light source 62, the control unit 55 causes the timing generator 34 to read only the lines A1, A2, and A3 (see FIG. 5), in which R and G pixels, on which red light or green light corresponding to the wavelength band of the special light is incident, are located. Furthermore, the control unit 55 controls the read timing in the read process in the timing generator 34 such that the exposure time of R and G pixels, on which red light or green light corresponding to the wavelength band of the special light is incident, becomes longer than the exposure time in the case where all the pixels are read. Consequently, it is possible to increase the luminance values of R and G pixels in the light receiving unit 28 that receives narrow-banded red light and green light that are the special light.

First Modification of First Embodiment

Next, the first modification of the first embodiment will be explained. In the first modification of the first embodiment, in the frame in which the pixel information is output by picking up an image of a subject that is irradiated with the special light emitted from the special light source 62, the pixel information on a line, in which pixels, on which the light corresponding to the wavelength band of the special light is incident, are located, is caused to be read a plurality of times, and in the image processing, an image is generated by summing the luminance values of the pixel information on the pixels, on which the light corresponding to the wavelength band of the special light is incident.

Figure 11:
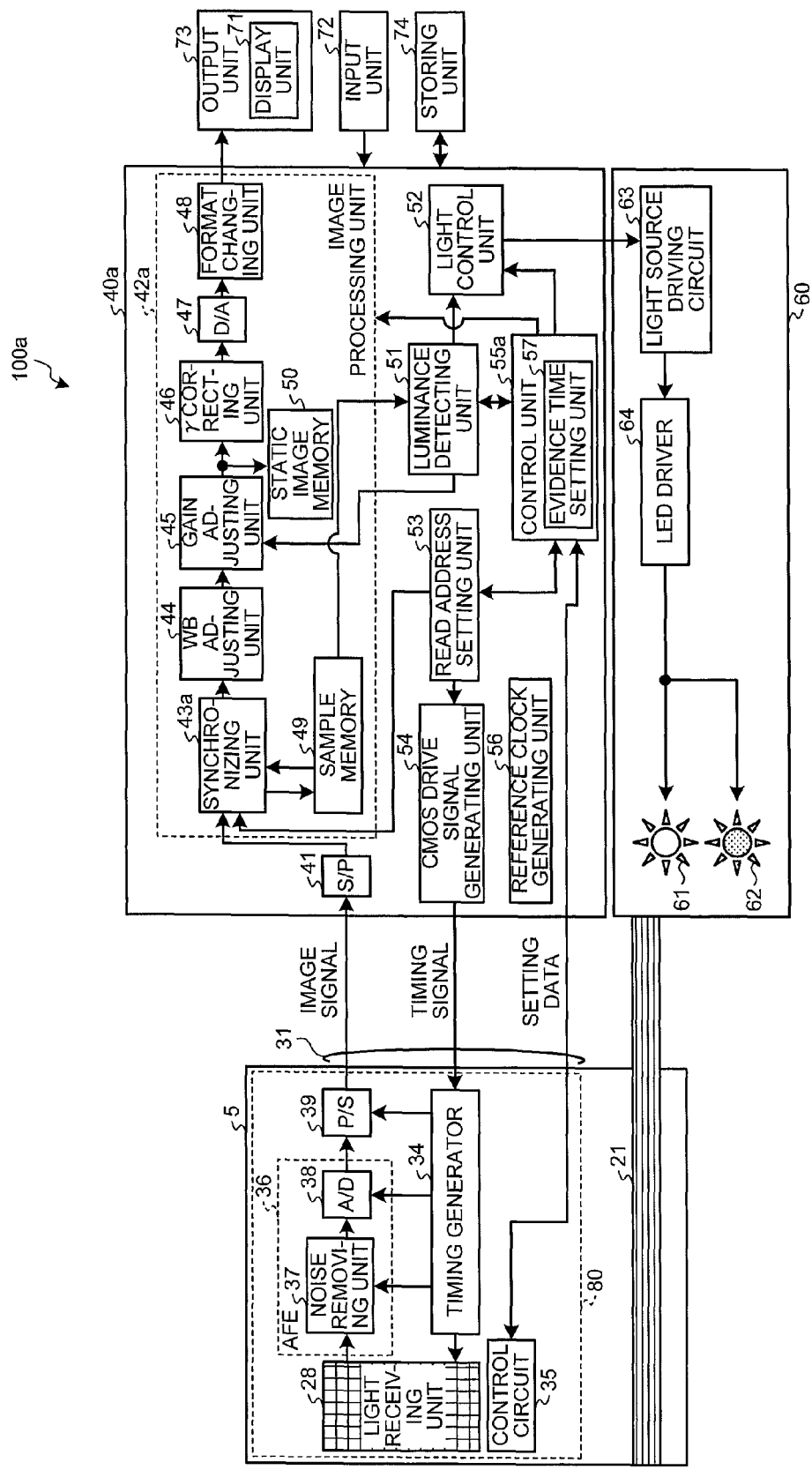
FIG. 11 is a block diagram illustrating a configuration of an endoscope system according to a first modification of the first embodiment.

FIG. 11 is a block diagram illustrating a configuration of an endoscope system according to the first modification of the first embodiment. As shown in FIG. 11, an endoscope system 100a according to the first modification of the first embodiment includes a control unit 55a instead of the control unit 55 shown in FIG. 3 and a control device 40a including an image processing unit 42a instead of the image processing unit 42.

In the frame in which the pixel information is output by picking up an image of a subject that is irradiated with the special light emitted from the special light source 62, the control unit 55a causes the timing generator 34 to read only the lines including G and B pixels, on which the light corresponding to the wavelength band of the NBI illumination light is incident, and read the pixel information on the lines, in which G and B pixels, on which the light corresponding to the wavelength band of the NBI illumination light is incident, are located, a plurality of times by controlling the read timing in the read process.

The image processing unit 42a includes a synchronizing unit 43a that generates image signals of a G image and a B image by summing the luminance values of the pixel information on the G and B pixels, respectively, in the frame in which the pixel information is output by picking up an image of a subject that is irradiated with the special light emitted from the special light source 62, and the image processing unit 42a generates an NBI image on the basis of a G image and an B image obtained by summing the luminance values of the pixel information on the G and B pixels, respectively.

Figure 12:
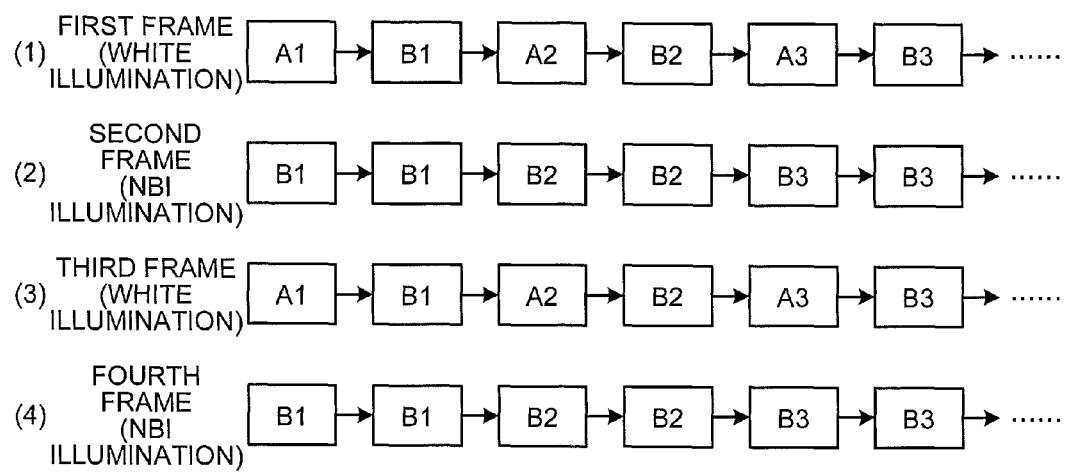
FIG. 12 is a diagram explaining a read process by a time generator illustrated in FIG. 11.
Figure 13:
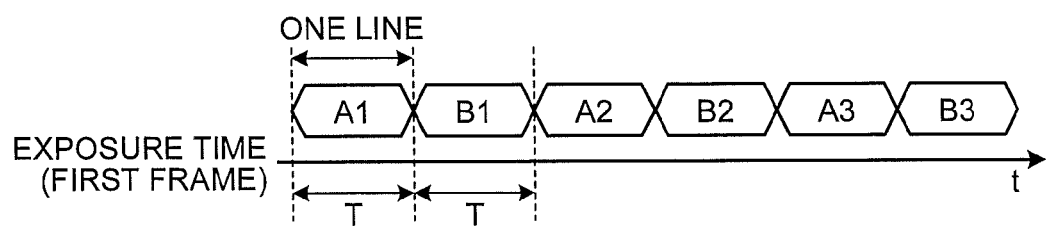
FIG. 13 is a diagram explaining an exposure time of each line in a light receiving unit in a frame corresponding to a time slot in which a white light source illustrated in FIG. 11 emits the white illumination light.
Figure 14:
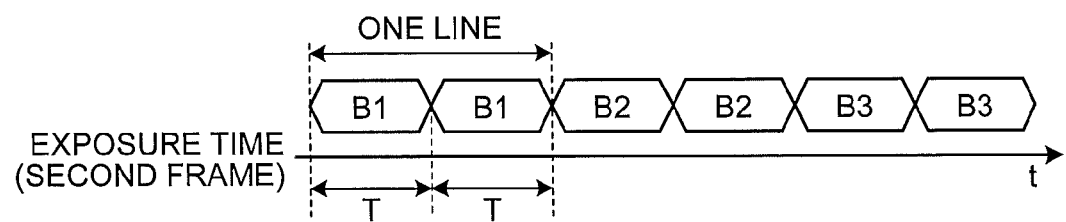
FIG. 14 is diagram explaining an exposure time of each line in the light receiving unit in a frame corresponding to a time slot in which a special light source illustrated in FIG. 11 emits the special light.

The read process in the first modification of the first embodiment will be explained with reference to FIG. 12 to FIG. 14. In a similar manner to the case shown in FIG. 4, in the first frame corresponding to the time slot in which the white light source 61 emits the white illumination light, the control unit 55a causes the timing generator 34 to perform the read process on all the lines following a predetermined direction. In the case where the light receiving unit 28 includes the pixel array shown in FIG. 5, as shown in FIG. 12(1), the control unit 55a causes the timing generator 34 to read the pixel information from the lines A1, B1, A2, B2, A3, and B3 in the sequence they appear in the sentence. At this time, as shown in FIG. 13, the exposure time of each line is time T.

In the second frame corresponding to the time slot in which the special light source 62 emits the NBI illumination light, the control unit 55a causes the timing generator 34 to read the pixel information on the lines B1, B2, and B3 (see FIG. 12(2)), in which only G pixels and B pixels, on which the light corresponding to the wavelength band of the NBI illumination light is incident, are located. At this time, because the timing generator 34 does not read half of all the lines, i.e., the lines A1, A2, and A3, the timing generator 34 reads the pixel information on the lines B1, B2, and B3 twice instead of reading the lines A1, A2, and A3. In other words, as shown in FIG. 14, in terms of the line B1, the control unit 55a causes the timing generator 34 to perform the read process for the exposure time T twice in succession by controlling the read timing in the read process in the timing generator 34. Next, in terms of the next line B2 also, the control unit 55a causes the timing generator 34 to perform the read process for the exposure time T twice in succession. In this manner, in the second frame, the timing generator 34 reads the pixel information from the lines B1, B1, B2, B2, B3, and B3 in the sequence they appear in the sentence. Then, the image processing unit 42a generates image signals of a G image and a B image by summing the luminance values of the pixel information on G and B pixels that are each read twice, respectively.

In the third frame corresponding to the time slot in which the white illumination light is emitted, in a similar manner to the first frame, the control unit 55a causes the timing generator 34 to read the pixel information from the lines A1, B1, A2, B2, A3, and B3 in the sequence they appear in the sentence (see FIG. 12(3)). Moreover, in the fourth frame corresponding to the time slot in which the NBI illumination light is emitted, in a similar manner to the second frame, the control unit 55a causes the timing generator 34 to read the pixel information from the lines B1, B1, B2, B2, B3, and B3 in the sequence they appear in the sentence (see FIG. 12(4)) and the image processing unit 42a generates image signals of a G image and a B image by summing the luminance values of the pixel information on G and B pixels that are each read twice, respectively. In the subsequent frames, in a similar manner, setting of the read timing and pixels as a read target is changed in accordance with the irradiation unit that emits light.

In this manner, in the endoscope system 100a according to the first modification of the first embodiment, in the frame in which the pixel information is output by picking up an image of a subject that is irradiated with the special light emitted from the special light source 62, only G and B pixels, on which the light corresponding to the wavelength band of the NBI illumination light is incident, are read twice in succession, and an NBI image is generated by summing the luminance values of the pixel information on G and B pixels that are each read twice, respectively. As a result, in the first modification of the first embodiment, in a similar manner to the first embodiment, the luminance values of G and B pixels are raised, therefore, a light NBI image can be obtained.

When the special light source 62 emits blue excitation light or violet excitation light having a shorter wavelength than blue as the special light in order to detect a labeling substance that is introduced into a subject and emits red fluorescence or green fluorescence or a fluorescent substance that is originally present in a living tissue and has a spectrum in the range of green or red, in the frame in which the pixel information is output by picking up an image of a subject that is irradiated with the special light emitted from the special light source 62, it is sufficient that the control unit 55a causes the timing generator 34 to read a line, in which R pixels and G pixels corresponding to the wavelength band of red fluorescence or green fluorescence as a target to be detected are located, twice in succession, and generates an image by summing the luminance values of the pixel information on the R and G pixels that are each read twice, respectively.

Moreover, when the special light source 62 emits the special light in two bands, i.e., narrow-banded red light and green light, in the frame in which the pixel information is output by picking up an image of a subject that is irradiated with the special light emitted from the special light source 62, it is sufficient that the control unit 55a causes the timing generator 34 to read a line, in which R pixels and G pixels corresponding to the wavelength band of red fluorescence or green fluorescence as a target to be detected are located, twice in succession, and generates an image by summing the luminance values of the pixel information on the R and G pixels that are each read twice, respectively.

Second Modification of First Embodiment

Next, the second modification of the first embodiment will be explained. In the second modification of the first embodiment, in the frame in which the pixel information is output by picking up an image of a subject that is irradiated with the special light emitted from the special light source 62, the timing generator sums the pixel information on a plurality of G and B pixels included in a block composed of a plurality of adjacent pixels and outputs the pixel information in units of blocks.

Figure 15:
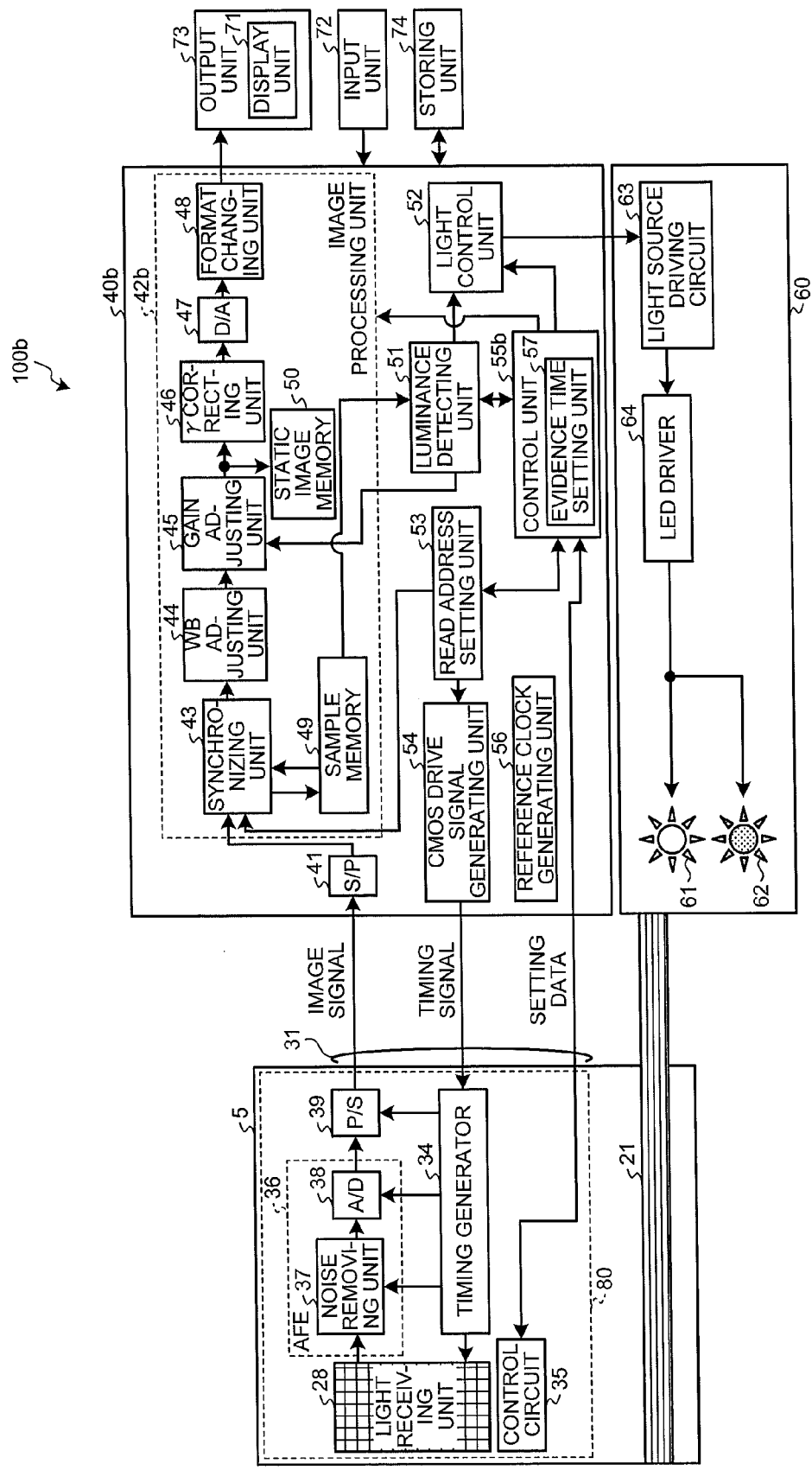
FIG. 15 is a block diagram illustrating a configuration of an endoscope system according to a second modification of the first embodiment.

FIG. 15 is a block diagram illustrating a configuration of an endoscope system according to the second modification of the first embodiment. As shown in FIG. 15, an endoscope system 100b according to the second modification of the first embodiment includes a control unit 55b instead of the control unit 55 shown in FIG. 3 and a control device 40b including an image processing unit 42b instead of the image processing unit 42.

In the frame in which the pixel information is output by picking up an image of a subject that is irradiated with the special light emitted from the special light source 62, in a similar manner to the control unit 55, the control unit 55b causes the timing generator 34 to read only G and B pixels, on which the light corresponding to the wavelength band of the NBI illumination light is incident, in a state where the exposure time is set longer than the exposure time in the case where all the pixels are read. Furthermore, the control unit 55b performs setting of the read address setting unit 53 to cause the timing generator 34 to perform binning-output to output the pixel information in units of blocks by summing the luminance values of a plurality of G and B pixels included in a block composed of a plurality of adjacent pixels, respectively. The image processing unit 42b generates an NBI image by using the pixel information on the G pixels and the B pixels that is output by performing binning-output.

Figure 16:
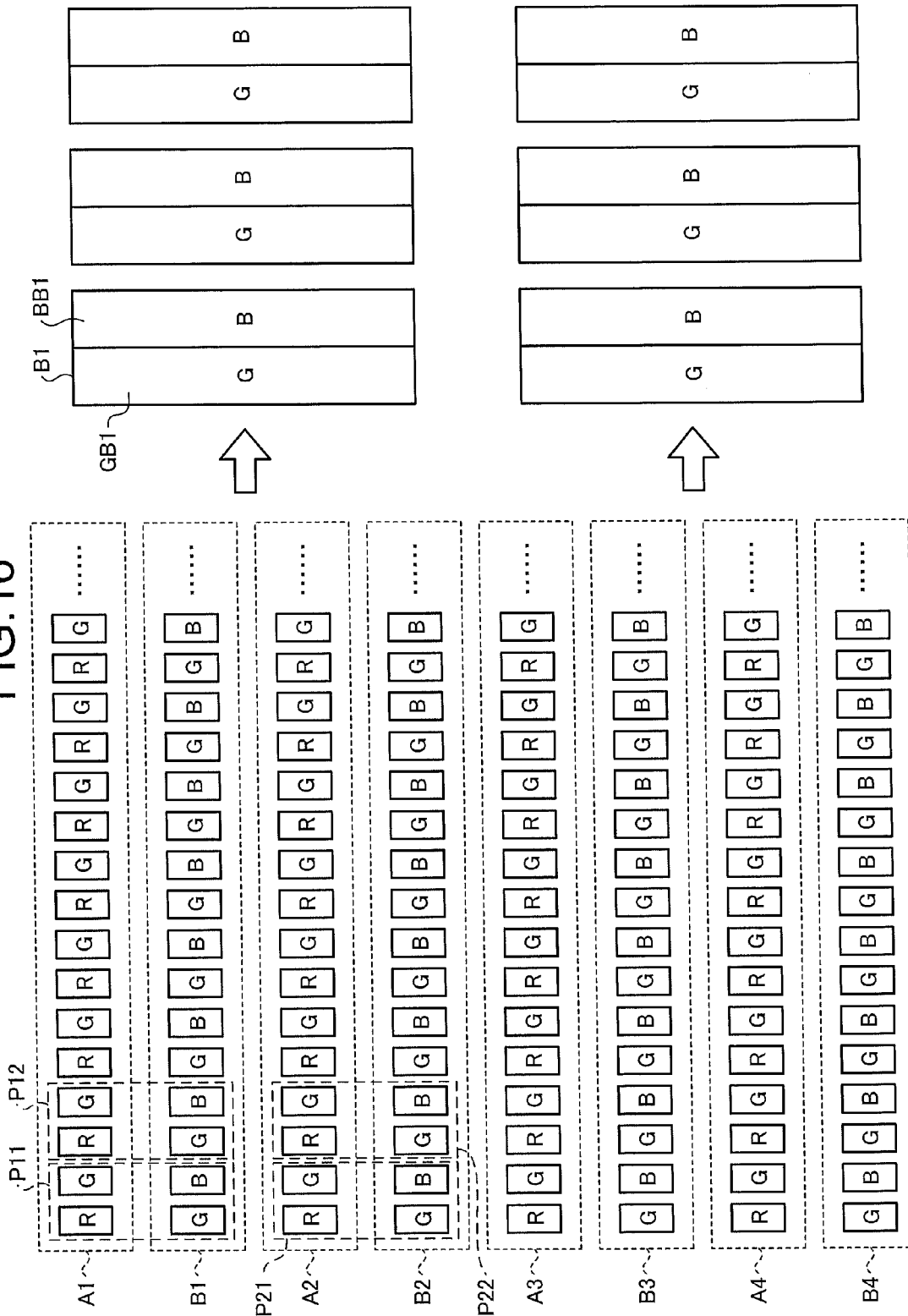
FIG. 16 is a diagram explaining a read process by a time generator illustrated in FIG. 15.

For example, a case is explained as an example in which four pixels, i.e., pixels P11 and P12 in the lines A1 and B1 and pixels P21 and P22 in the lines A2 and B2, are set as one block as shown in the left figure in FIG. 16. In this case, in the frame in which the pixel information is output by picking up an image of a subject that is irradiated with the special light emitted from the special light source 62, as shown in the right figure in FIG. 16, the timing generator 34 reads the pixel information on G and B pixels in the lines B1 and B2 in the four pixels P11, P12, P21, and P22, and performs binning-output to output the pixel information as pixel information GB1 and BB1 by summing the luminance values of the read G and B pixels, respectively. In this case, R and G pixels in the lines A1 and A2 are not read and are not output by performing binning-output. In terms of other blocks, in a similar manner, the pixel information is output by performing binning-output by summing the luminance values of G and B pixels in the lines, in which only G and B pixels are located, respectively, for each pixel.

In this manner, in the second modification of the first embodiment, in the frame in which the pixel information is output by picking up an image of a subject that is irradiated with the special light emitted from the special light source 62, only G and B pixels, on which the light corresponding to the wavelength band of the NBI illumination light is incident, are read for the exposure time longer than the exposure time in the case where all the pixels are read, and moreover, the pixel information on G and B pixels is output in units of blocks each composed of a plurality of pixels by performing binning-output, whereby the luminance values of G pixels and B pixels are raised.

In the frame in which the pixel information is output by picking up an image of a subject that is irradiated with the special light emitted from the special light source 62, the timing generator 34 may be caused to read only G and B pixels twice in succession as explained in the first modification in the first embodiment, and output the pixel information on G and B pixels in units of blocks by performing binning-output on the basis of the summed luminance values of the G and B pixels that are each read twice.

Moreover, when the special light source 62 emits blue excitation light or violet excitation light having a shorter wavelength than blue to a substance that emits fluorescence included in the wavelength band of red light and green light, in the frame in which the pixel information is output by picking up an image of a subject that is irradiated with the special light emitted from the special light source 62, it is sufficient that the control unit 55b causes the timing generator 34 to perform binning-output to output the pixel information on R and G pixels in units of blocks. Moreover, the same is true for the case where the special light source 62 emits the special light in two bands, i.e., narrow-banded red light and green light.

Second Embodiment

Next, the second embodiment will be explained. In the second embodiment, in the frame in which the pixel information is output by picking up an image of a subject that is irradiated with the special light emitted from the special light source 62, a noise removing image indicating the output unevenness distribution in the entire pixel region is obtained and noise removal is performed, thereby obtaining an appropriate special image.

Figure 17:
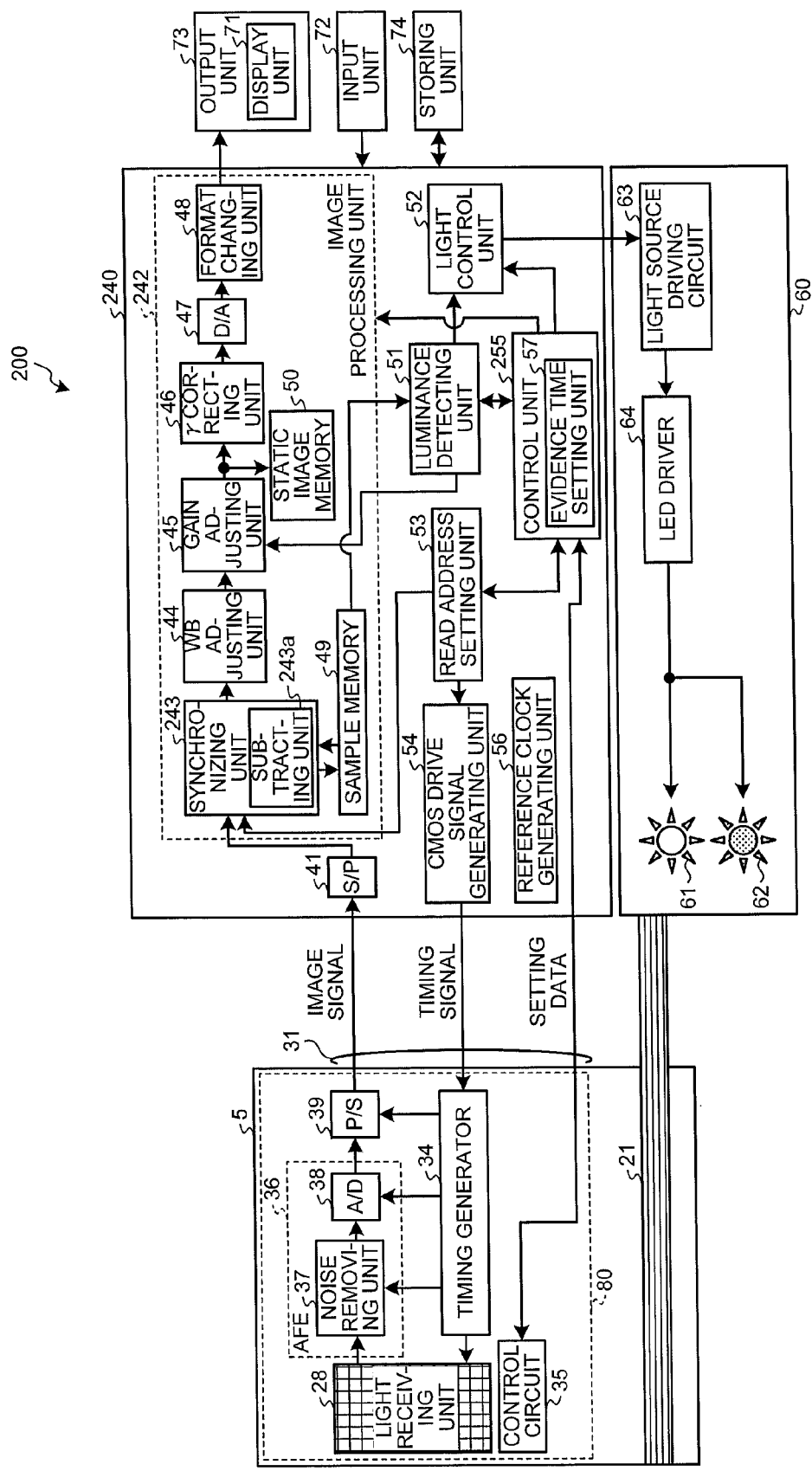
FIG. 17 is a block diagram illustrating a configuration of an endoscope system according to a second embodiment.

FIG. 17 is a block diagram illustrating a configuration of an endoscope system according to the second embodiment. As shown in FIG. 17, an endoscope system 200 according to the second embodiment includes a control unit 255 instead of the control unit 55 shown in FIG. 3 and a control device 240 including an image processing unit 242 instead of the image processing unit 42.

In the frame in which the pixel information is output by picking up an image of a subject that is irradiated with the special light emitted from the special light source 62, the control unit 255 causes the timing generator 34 to read only the pixel information on R pixels in a line, in which R pixels, on which the light corresponding to the wavelength band of the special light is not incident, are located, and read all the G and B pixels in a line, in which G and B pixels, on which the light corresponding to the wavelength band of the NBI illumination light that is the special light is incident, are located. Because the light corresponding to the wavelength band of the special light is not incident on R pixels, an R image can be used as the noise removing image that reflects a dark current component and a fixed pattern component.

A synchronizing unit 243 of the image processing unit 242 includes a subtracting unit 243a that subtracts the luminance value of the pixel information on an R pixel located closest to G and B pixels from the luminance values of the pixel information on the G and B pixels for each G and B pixels in the frame in which the pixel information is output by picking up an image of a subject that is irradiated with the special light emitted from the special light source 62. The image processing unit 242 generates an image on the basis of the subtraction process result by the subtracting unit 243a.

In the second embodiment, R pixels read to form the noise removing image are one fourth of the total number of the pixels, therefore, the read time to read the lines A1, A2, and A3 (see FIG. 5), in which R pixels are located, can be shorter than the read time to read the lines B1, B2, and B3, in which G and B pixels are located. Thus, the exposure time of G and B pixels, on which the light corresponding to the wavelength band of the special light is incident, is set to be longer than the exposure time in the case where all the pixels are read by a given amount.

Figure 18:
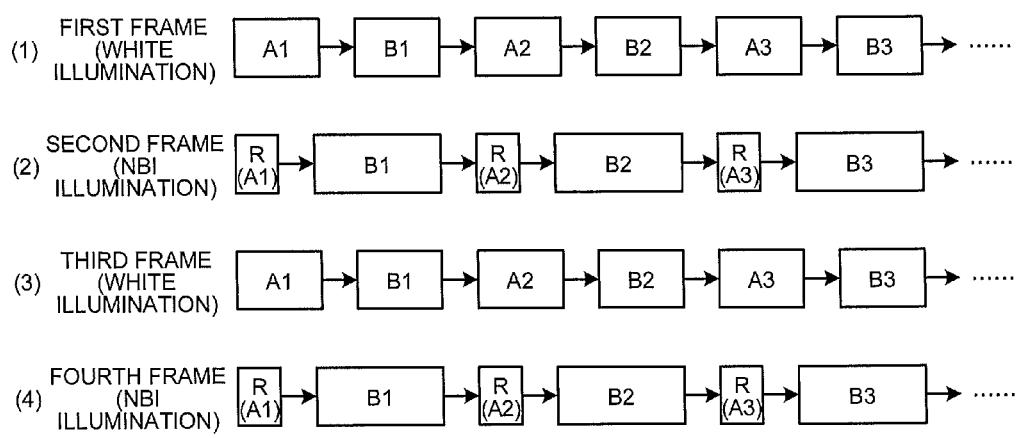
FIG. 18 is a diagram explaining a read process by a timing generator illustrated in FIG. 17.
Figure 19:
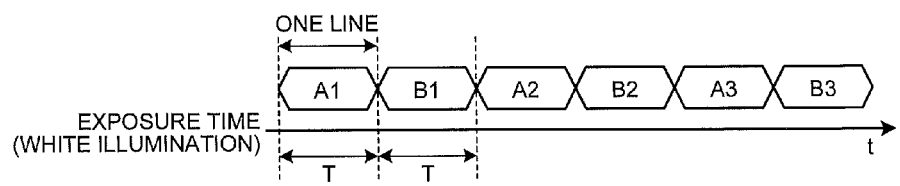
FIG. 19 is a diagram explaining an exposure time of each line in a light receiving unit in a frame corresponding to a time slot in which a white light source illustrated in FIG. 17 emits the white illumination light.
Figure 20:
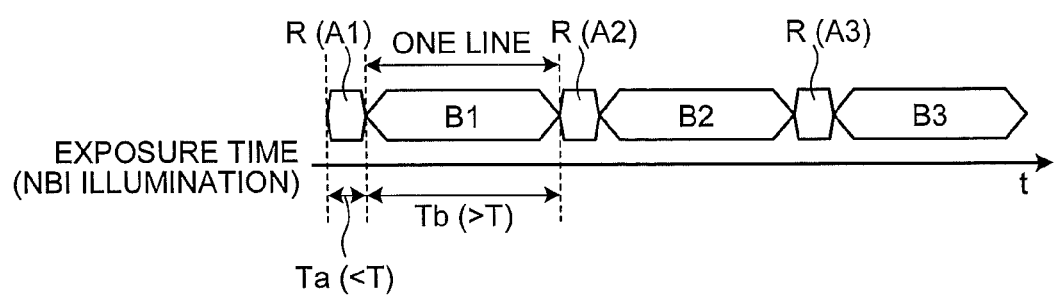
FIG. 20 is diagram explaining an exposure time of each line in the light receiving unit in a frame corresponding to a time slot in which a special light source illustrated in FIG. 17 emits the special light.

Next, the read process according to the second embodiment will be explained with reference to FIG. 18 to FIG. 20. In a similar manner to the first embodiment, in the first frame corresponding to the time slot in which the white light source 61 emits the white illumination light, the control unit 255 causes the timing generator 34 to perform the read process on all the lines following a predetermined direction. For example, as shown in FIG. 18(1), the control unit 255 causes the timing generator 34 to read the pixel information from the lines A1, B1, A2, B2, A3, and B3 in the sequence they appear in the sentence. At this time, as shown in FIG. 19, the exposure time corresponding to each line is time T.

In the second frame corresponding to the time slot in which the special light source 62 emits the NBI illumination light, in terms of the lines A1, A2, and A3 (see FIG. 18(2)), in which only R pixels, on which the light corresponding to the wavelength band of the NBI illumination light is not incident, are located, the control unit 255 causes the timing generator 34 to read only the pixel information on R pixels. In terms of the lines B1, B2, and B3 (see FIG. 18(2)), in which only G pixels and B pixels, on which the light corresponding to the wavelength band of the NBI illumination light is incident, are located, the control unit 255 causes the timing generator 34 to read the pixel information on all of G pixels and B pixels. At this time, because only R pixels are read from the lines A1, A2, and A3, the control unit 255 controls the read timing of the timing generator 34 such that the exposure time of the lines B1, B2, and B3 (see FIG. 18(2)), in which G and B pixels are located, becomes longer than the exposure time in the case where all the pixels are read by a given amount. For example, in terms of the lines A1, A2, and A3, in which R and G pixels are located, among two lines, only R pixels are read, therefore, as shown in FIG. 20, exposure time Ta, which is shorter than the exposure time T per line in the case where all the pixels are read, is sufficient. Thus, as shown in FIG. 20, exposure time Tb of the lines B1, B2, and B3, in which G and B pixels are located, is made longer than the exposure time T per line shown in FIG. 19 by a given amount.

In this manner, in the second frame, the pixel information on R, G, and B pixels is read from R pixels in the line A1, the line B1, R pixels in the line A2, and the line B2 in the sequence they appear in the sentence, thereby obtaining G and B images composing the NBI image and an R image composing the noise removing image. In the frame in which the pixel information is output by picking up an image of a subject that is irradiated with the special light emitted from the special light source 62, the image processing unit 242 generates an image after subtracting the luminance values of R pixels of an R image that is the noise removing image from the luminance values of G and B pixels of G and B images composing the NBI image by the subtracting unit 243a. The subtracting unit 243a performs noise removal for each line by subtracting the luminance values of R pixels in the line A1 from the luminance values of G and B pixels in the next line B1. When the noise is removed in this manner, the process can be performed by using only a line memory without providing a frame memory.

In a similar manner, in the third frame corresponding to the time slot in which the white illumination light is emitted, as shown in FIG. 18(3), in a similar manner to the first frame, the control unit 255 causes the timing generator 34 to read the pixel information from the lines A1, B1, A2, B2, A3, and B3 in the sequence they appear in the sentence. Moreover, in the fourth frame corresponding to the time slot in which the NBI illumination light is emitted, as shown in FIG. 18(4), in a similar manner to the second frame, the control unit 255 causes the timing generator 34 to read the pixel information from R pixels in the line A1, the line B1, R pixels in the line A2, and the line B2 in the sequence they appear in the sentence, thereby obtaining G and B images composing the NBI image and an R image composing the noise removing image.

In a similar manner to the second frame, the image processing unit 242 generates an image after subtracting the luminance values of R pixels of an R image that is the noise removing image from the luminance values of G and B pixels of G and B images composing the NBI image by the subtracting unit 243a.

In this manner, in the second embodiment, because the exposure time of a line, in which G and B are located, is made longer than the exposure time in the case where all the pixels are read, it is possible to increase the luminance values of G and B pixels in the light receiving unit 28, which receives blue light and green light, without providing a dedicated image pickup element, which is conventionally needed, therefore, a light NBI image can be obtained.

Furthermore, in the second embodiment, in the frame in which the pixel information is output by picking up an image of a subject that is irradiated with the special light emitted from the special light source 62, the pixel information on an R image is also obtained in addition to that on G and B images composing the NBI image for forming the noise removing image indicating the output unevenness distribution of the entire pixel region, and a dark current component and a fixed pattern component distributed throughout the entire pixel region are removed by calculating the difference from the luminance values of G and B images. Thus, the dynamic range of the entire image can be appropriately expanded.

In the second embodiment, a case is explained as an example in which the image processing unit 242 removes the noise in units of lines, however, noise removal may be performed for each frame by storing the luminance values of R pixels of an R image that is the noise removing image in units of frames and subtracting the luminance values of the R pixels of the R image that is the noise removing image from the luminance values of G and B pixels of G and B images composing the NBI image in units of frames.

Moreover, when the special light source 62 emits blue excitation light or near-ultraviolet excitation light that excites a fluorescent substance that is originally present in a living tissue or a labeling substance that is introduced from outside and emits fluorescence, the lines A1, A2, and A3 (see FIG. 5), in which R and G pixels, on which red or green that is excited and generated by the excitation light is incident, are located, are read after a long time exposure. Next, in the lines B1, B2, and B3 (see FIG. 5), in which B pixels, on which blue light that does not correspond to the wavelength band of the special light is incident, are located, it is sufficient that the control unit 255 causes only the B pixels to be read after a short time exposure as the noise removing image. Then, the image processing unit 242 generates an image after subtracting the luminance values of the B pixels of the noise removing image from the luminance values of the R and G pixels composing an image by the subtracting unit 243a. Moreover, the same is true for the case where the special light source 62 emits the special light in two bands, i.e., narrow-banded red light and green light.

Third Embodiment

Next, the third embodiment will be explained. In the third embodiment, the white light source is turned off for a certain period of time in part of the time slot in each time slot in which the white light source emits the white illumination light and the pixel information on part of all the pixels, which are obtained by decimating the pixels at predetermined intervals, is read for removing the noise to correspond to the turn-off period of the white light source 61.

Figure 21:
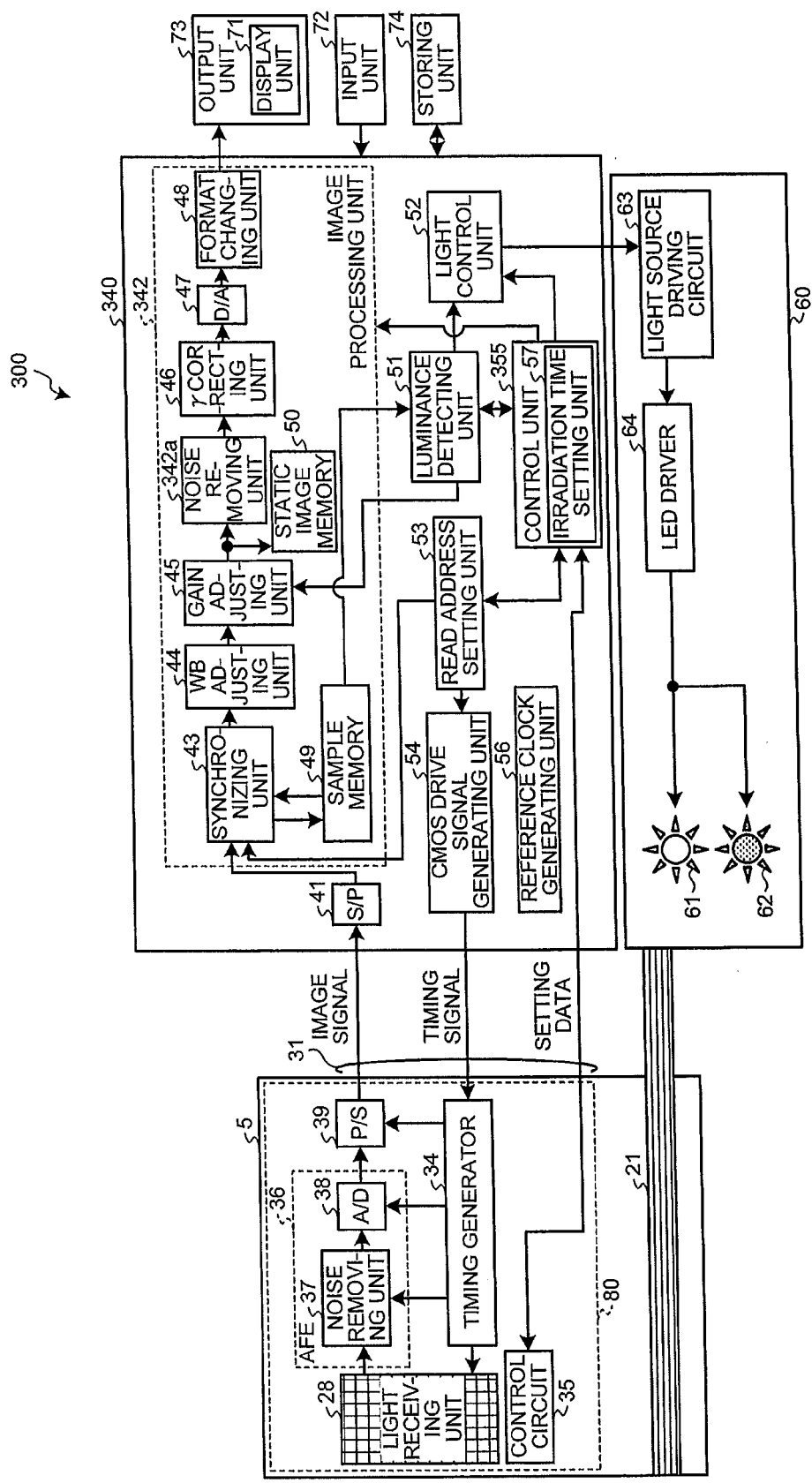
FIG. 21 is a block diagram illustrating a configuration of an endoscope system according to a third embodiment.

FIG. 21 is a block diagram illustrating a configuration of an endoscope system according to the third embodiment. As shown in FIG. 21, an endoscope system 300 according to the third embodiment includes a control unit 355 instead of the control unit 55 shown in FIG. 3 and a control device 340 including an image processing unit 342 instead of the image processing unit 42.

In part of the time slot in each time slot in which the white light source 61 emits the white illumination light, the control unit 355 turns off the white light source 61 for a certain period of time and causes the timing generator 34 to read the pixel information on part of all the pixels, which are obtained by decimating the pixels at predetermined intervals, as the noise removing image to correspond to the turn-off period of the white light source 61.

The image processing unit 342 includes a noise removing unit 342a that removes the noise of the pixel information by subtracting the luminance value of a pixel of the noise removing image located closest to G and B pixels from the luminance values of the pixel information on the G and B pixels for each pixel information on G and B pixels, on which the light corresponding to the wavelength band of the special light from the special light source 62 is incident, in the frame in which the pixel information is output by picking up an image of a subject that is irradiated with the special light emitted from the special light source 62. The image processing unit 342 generates an image on the basis of the pixel information from which the noise is removed by the noise removing unit 342a.

Figure 22:
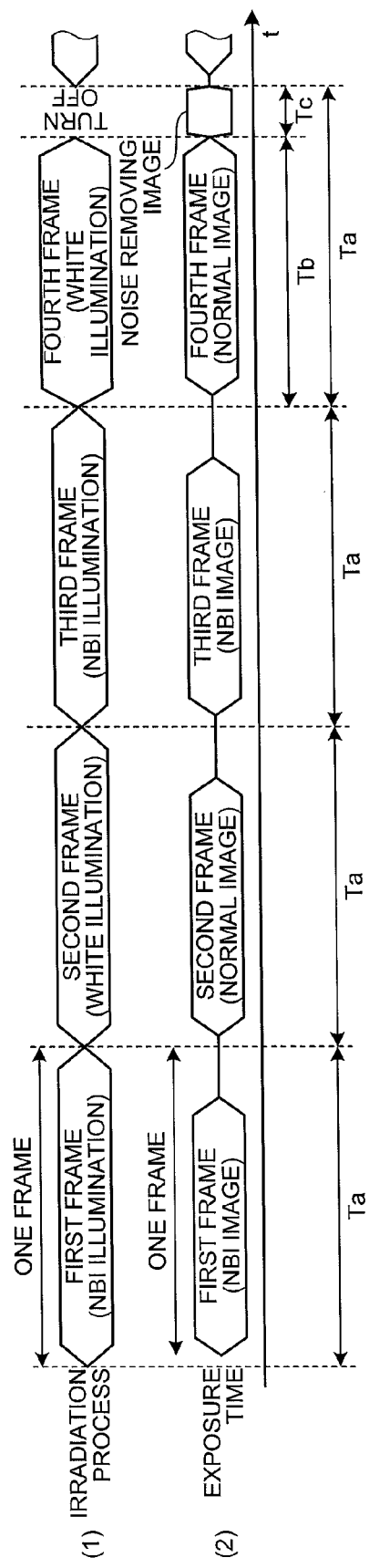
FIG. 22 is a diagram explaining an irradiation process by a white light source and a special light source illustrated in FIG. 21 and an exposure time corresponding to each frame in a light receiving unit.

Next, the illumination control process and the read process according to the third embodiment will be explained with reference to FIG. 22. As shown in FIG. 22(1), the control unit 355 turns off the white light source 61, for example, during a period Tc that is part of an irradiation period Ta corresponding to the fourth frame. In a period Tb in the irradiation period Ta corresponding to the fourth frame, the control unit 355 causes the timing generator 34 to read the pixel information on all the pixels in the light receiving unit 28 for a normal image. In the period Tc in the irradiation period Ta corresponding to the fourth frame, the control unit 355 causes the timing generator 34 to read the pixel information on part of all the pixels, which are obtained by decimating the pixels at predetermined intervals, for removing the noise.

In the period Tc, both the white light source 61 and the special light source 62 are off, therefore, light is supplied into a subject, in which the tip portion 5 is introduced, only from the light sources. Therefore, in the period Tc, light is not incident on any pixel, thus, the pixel information in this case can be used as the noise removing image that reflects a dark current component and a fixed pattern component. For removing the noise, for example, the pixel information on a line obtained by excluding one of the adjacent two lines may be used or the pixel information on only R pixels among R, G, and B pixels may be read. The image processing unit 342 generates an image after subtracting the luminance values of the pixels of the decimated read image for removing the noise from the luminance values of G and B pixels composing the NBI image by the noise removing unit 342a. As shown in FIG. 22, when the pixel signals of the pixels of the noise removing image are obtained in units of frames, the control unit 355 causes the static image memory 50 to store the noise removing image when the illumination light is off. Then, the noise removing unit 342a subtracts the luminance values of the pixels of the decimated read image for removing the noise from the luminance values of G and B pixels composing the NBI image to be output next. Alternatively, the noise removing unit 342a subtracts the luminance values of the pixels of the decimated read image for removing the noise from the luminance values of R, G, and B pixels composing a normal image to be output next. In the third embodiment, an image from which the noise is removed for each frame is obtained.

In this manner, in the third embodiment, the pixel information when the light sources are turned off is obtained as the noise removing image indicating the output unevenness distribution in the entire pixel region and the difference from the luminance values of G and B images composing the NBI image is calculated, whereby the dynamic range of the entire image can be appropriately expanded in a similar manner to the second embodiment.

In the third embodiment, a case is explained as an example in which the image processing unit 342 removes the noise in units of frames, however, noise removal may be performed for each line by storing the luminance values of pixels composing the noise removing image in units of lines and subtracting the luminance values of the pixels of the noise removing image from the luminance values of G and B pixels of G and B images composing the NBI image in units of lines.

Moreover, in the third embodiment, in a similar manner to the first embodiment, in the frame in which the pixel information is output by picking up an image of a subject that is irradiated with the special light emitted from the special light source 62, the exposure time of a line in which G and B pixels are located may be made longer than the exposure time T in the case where all the pixels are read by avoiding reading the pixel information on a line in which R pixels are located, or a line in which G and B pixels are located may be read twice. Furthermore, the read pixel information on G and B pixels may be output for each block by performing binning-output. Moreover, in the third embodiment, the NBI image is explained as an example, however, it can of course be applied also to the case of fluorescent observation.

Figure 23:
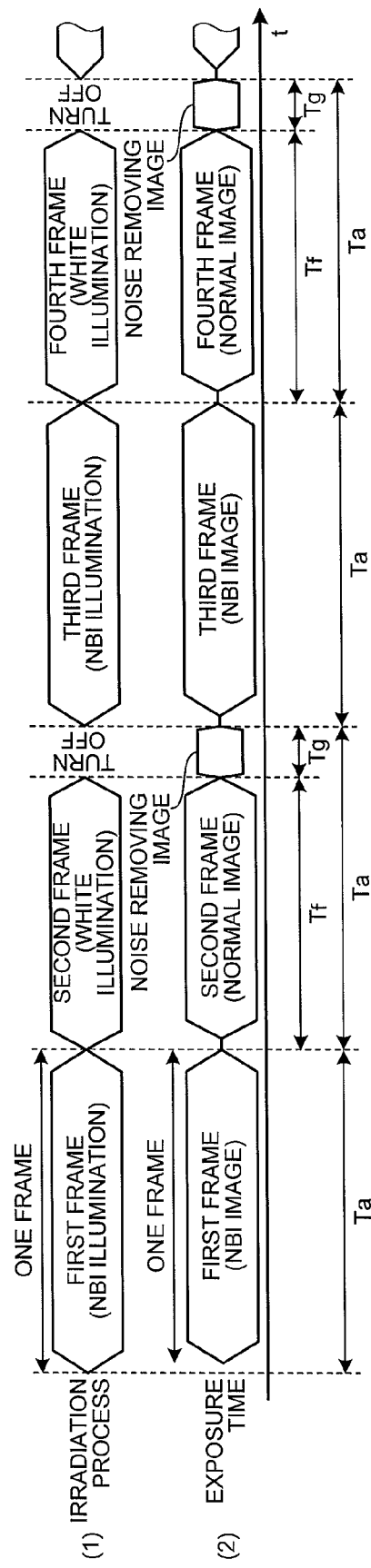
FIG. 23 is a diagram explaining another example of an irradiation process by the white light source and the special light source illustrated in FIG. 21 and an exposure time corresponding to each frame in the light receiving unit.

Moreover, as shown in FIG. 23(1), the control unit 355 may turn off the white light source 61 at regular time intervals for each time slot in which the white light source 61 emits the white light. Then, as shown in FIG. 23(2), the control unit 355 may cause the timing generator 34 to read the pixel information on part of all the pixels, which are obtained by decimating the pixels at predetermined intervals, for removing the noise in each turn-off period Tg of the white light source 61. In this case, in the frame corresponding to the time slot in which the white illumination light is emitted, because the turn-off period Tg that is part of the period Ta becomes the exposure time for the noise removing image, the exposure time for a normal image becomes a remaining period Tf obtained by subtracting the turn-off period Tg from the irradiation period Ta. At that time, because the exposure time for the NBI image, the exposure time for a normal image, and the exposure time for the noise removing image are different from each other, weighting is performed according to the exposure time.

Moreover, in the first to third embodiments, a case is explained as an example in which the pixel information is read for each line in the horizontal direction in the light receiving unit 28 as shown in FIG. 5 from top to bottom, however, obviously, the pixel information may be read for each line in the vertical direction from left to right.

Moreover, the present embodiment can improve the efficiency by applying it also to image pickup apparatus in a digital camera, a digital single-lens reflex camera, a digital video camera, a camera-equipped mobile terminal, or the like without being limited to an endoscope system.

Additional advantages and modifications will readily occur to those skilled in the art. Therefore, the invention in its broader aspects is not limited to the specific details and representative embodiments shown and described herein.

Accordingly, various modifications may be made without departing from the scope of the general inventive concept as defined by the appended claims and their equivalents.

What is claimed is:

1. An image pickup apparatus comprising:
   a first irradiation unit that emits first light to a subject;
   a second irradiation unit that emits second light that has a wavelength band different from that of the first light, to the subject;
   an image pickup unit that is capable of outputting, as pixel information, an electrical signal after photoelectric conversion from a pixel arbitrarily designated as a read target among a plurality of pixels for imaging;
   a setting unit that is capable of arbitrarily setting a pixel as the read target and a read order in the image pickup unit;
   a control unit that controls irradiation processes in the first irradiation unit and the second irradiation unit and changes the pixel as the read target and the read order set by the setting unit according to a type of an irradiation unit that emits light;
   a reading unit that reads the pixel information by causing the pixel information to be output from the pixel set as the read target by the setting unit among the plurality of pixels for imaging in the image pickup unit, in accordance with the read order according to setting in the setting unit;
   an image processing unit that generates an image from the pixel information read by the reading unit; and
   a display unit that displays the image generated by the image processing unit, wherein
   in a frame in which the image pickup unit picks up an image of the subject irradiated with the second light emitted from the second irradiation unit to output the pixel information, the control unit performs control such that the reading unit does not read the pixel information from a first pixel on which light corresponding to the wavelength band of the second light is not incident, a second pixel on which light corresponding to the wavelength band of the second light is incident is exposed and the reading unit reads the pixel information from the exposed second pixel during a period for exposing and reading the first pixel and during a period for reading the pixel information from the second pixel.

2. The image pickup apparatus according to claim 1, wherein the second light is light having the wavelength band narrower than that of the first light.

3. The image pickup apparatus according to claim 1, wherein in a frame in which the pixel information is output by picking up an image of the subject irradiated with the second light emitted from the second irradiation unit, the control unit causes the reading unit to read the pixel information on a line in which only the second pixel is located.

4. The image pickup apparatus according to claim 1, wherein in a frame in which the pixel information is output by picking up an image of the subject irradiated with the second light emitted from the second light source, the control unit controls a read timing of the reading unit such that an exposure time of the second pixel becomes longer than an exposure time in a case where all the pixels are read.

5. The image pickup apparatus according to claim 1, wherein
   the pixel information includes a luminance value,
   in a frame in which the pixel information is output by picking up an image of the subject irradiated with the second light emitted from the second irradiation unit, the control unit causes the reading unit to read the pixel information on the second pixel a plurality of times, and in a frame in which the pixel information is output by picking up an image of the subject irradiated with the second light emitted from the second irradiation unit, the image processing unit generates the image by summing luminance values of the pixel information on the second pixel that is read a plurality of times.

6. The image pickup apparatus according to claim 1, wherein the control unit sets the setting unit to cause the reading unit to sum luminance values of a plurality of second pixels included in a block that has a plurality of pixels adjacent to each other so as to be output in units of blocks.

7. The image pickup apparatus according to claim 1, wherein
   in a frame in which the pixel information is output by picking up an image of the subject irradiated with the second light emitted from the second irradiation unit, the control unit causes the reading unit to read only the pixel information on the first pixel for a first line on which the first pixel is located, light corresponding to the wavelength band of the second light being not incident on the first pixel, and causes the reading unit to read all of second pixels for a second line on which the second pixels are located, light corresponding to the wavelength band of the second light being incident on the second pixels, and
   the image processing unit further includes a subtracting unit that subtracts a luminance value of the pixel information on the first pixel located closest to the second pixel from a luminance value of the pixel information on the second pixel, for each of the second pixels, in a frame in which the pixel information is output by picking up an image of the subject irradiated with the second light emitted from the second irradiation unit, and generates the image on a basis of a subtraction process result by the subtracting unit.

8. The image pickup apparatus according to claim 7, wherein in a frame in which the pixel information is output by picking up an image of the subject irradiated with the second light emitted from the second light source, the control unit controls a read timing of the reading unit such that an exposure time of the second pixel becomes longer than an exposure time in a case where all the pixels are read.

9. The image pickup apparatus according to claim 1, wherein
   in part of each time slot in which the first irradiation unit emits the first illumination light, the control unit turns off the first irradiation unit for a certain period of time and causes the reading unit to read the pixel information on a part of all the pixels which is obtained by decimating the pixels at a predetermined interval according to a turn-off period of the first irradiation unit to remove noise, and
   the image processing unit includes a noise removing unit that removes noise of pixel information by subtracting a luminance value of the pixel information of a pixel for removing noise located closest to the second pixel from a luminance value of the pixel information on the second pixel, in a frame in which the pixel information is output by picking up an image of the subject irradiated with the second light emitted from the second irradiation unit, and generates the image on a basis of the pixel information from which noise is removed by the noise removing unit.

10. The image pickup apparatus according to claim 9, wherein the control unit turns off the first irradiation unit for a certain period of time in each time slot in which the first irradiation unit emits the first light.

11. The image pickup apparatus according to claim 1, wherein the control unit causes the reading unit to read the pixel information in units of lines in sequence following a predetermined direction.

12. The image pickup apparatus according to claim 1, wherein
the control unit causes the first irradiation unit and the second irradiation unit to emit light alternately, and further includes an irradiation time setting unit that sets an irradiation time for single irradiation by each of the first irradiation unit and the second irradiation unit according to a time required for outputting the pixel information corresponding to one image by the image pickup unit.

13. The image pickup apparatus according to claim 1, wherein
the second irradiation unit emits light included in a wavelength band of a green light and a blue light, as the second light, and
in a frame in which the second irradiation unit emits the second light, the control unit causes the reading unit to read pixel information on a pixel on which the green light and the blue light corresponding to the wavelength band of the second light is incident.

14. The image pickup apparatus according to claim 1, wherein
the second irradiation unit emits, as the second light, an excitation light that excites fluorescence substance, the excitation light being included in a wavelength band of a red light and a green light, and
in a frame in which the second irradiation unit emits the excitation light, the control unit causes the reading unit to read pixel information on a pixel on which light of a red fluorescence or a green fluorescence corresponding to the excitation light is incident.

15. The image pickup apparatus according to claim 1, wherein
the second irradiation unit emits light included in a wavelength band of a red light and a green light, as the second light, and
in a frame in which the second irradiation unit emits the second light, the control unit causes the reading unit to read pixel information on a pixel on which the red light or the green light corresponding to the wavelength band of the second light is incident.

* * * * *